(12) United States Patent
Takahashi et al.

(10) Patent No.: US 8,023,118 B2
(45) Date of Patent: Sep. 20, 2011

(54) ANALYZER FOR ABSORPTION SPECTROMETRY OF IMPURITY CONCENTRATION CONTAINED IN LIQUID USING EXCITING LIGHT

(75) Inventors: Eiji Takahashi, Kobe (JP); Ryo Katayama, Kobe (JP); Masato Kannaka, Kobe (JP); Hiroyuki Takamatsu, Kobe (JP)

(73) Assignee: Kobe Steel, Ltd., Hyogo (JP)

( * ) Notice: Subject to any disclaimer, the term of this patent is extended or adjusted under 35 U.S.C. 154(b) by 314 days.

(21) Appl. No.: 12/224,302

(22) PCT Filed: Mar. 16, 2007

(86) PCT No.: PCT/JP2007/055382
§ 371 (c)(1),
(2), (4) Date: Aug. 22, 2008

(87) PCT Pub. No.: WO2007/119399
PCT Pub. Date: Oct. 25, 2007

(65) Prior Publication Data
US 2009/0027654 A1    Jan. 29, 2009

(30) Foreign Application Priority Data

Mar. 22, 2006  (JP) ................................. 2006-078740
Dec. 4, 2006   (JP) ................................. 2006-327093

(51) Int. Cl.
*G01B 9/02*    (2006.01)
*G01J 3/45*    (2006.01)
*G01N 21/00*   (2006.01)

(52) U.S. Cl. ........................................ 356/451; 356/432

(58) Field of Classification Search ................... 356/432, 356/450, 451, 498, 503, 504
See application file for complete search history.

(56) References Cited

U.S. PATENT DOCUMENTS
3,680,962 A * 8/1972 Hayakawa .................. 356/338
(Continued)

FOREIGN PATENT DOCUMENTS
EP    0 310 740 A3    4/1989
(Continued)

OTHER PUBLICATIONS

Takahashi, Eiji, et al., "High Sensitivity Light Absorption Analysis by Laser Interferometric Photo-Thermal Conversion Method", 54th Annual Meeting of the Japan Society for Analytical Chemistry, H1010, 2005, p. 186, in Japanese with English translation.

(Continued)

*Primary Examiner* — Michael A Lyons
(74) *Attorney, Agent, or Firm* — Stites & Harbison PLLC; Juan Carlos A. Marquez, Esq.

(57) ABSTRACT

The concentration of impurities contained in ultrapure water or press water can be efficiently analyzed with high precision. A portion of a liquid to be measured is introduced into an absorption spectrometric portion from a predetermined line. The liquid is irradiated with exciting light from an exciting light irradiation system, and a measurement object region in which a photothermal effect of the impurities in the liquid is produced by the irradiation is irradiated with measuring light from a measuring light irradiation system. A change in phase of the measuring light is detected by a predetermined optical system and a photodetector, and the impurity concentration in the liquid is determined on the basis of the change in phase.

8 Claims, 12 Drawing Sheets

U.S. PATENT DOCUMENTS

| | | | | |
|---|---|---|---|---|
| 3,734,601 | A * | 5/1973 | Heiss | 356/246 |
| 5,739,902 | A | 4/1998 | Gjelsnes et al. | |
| 7,105,354 | B1 * | 9/2006 | Shimoide et al. | 436/164 |
| 7,522,287 | B2 * | 4/2009 | Takahashi et al. | 356/503 |
| 2001/0022657 | A1 * | 9/2001 | Autrey et al. | 356/432 |
| 2007/0240495 | A1 | 10/2007 | Hirahara | |

FOREIGN PATENT DOCUMENTS

| | | | |
|---|---|---|---|
| EP | 1 338 890 A1 | | 8/2003 |
| EP | 1 691 189 A2 | | 8/2006 |
| JP | 60-144644 | | 1/1984 |
| JP | 3306828 | | 6/1994 |
| JP | 2001-153855 | | 11/1999 |
| JP | 2000002675 A | * | 1/2000 |
| JP | 2001-242136 | | 2/2000 |
| JP | 2003-149135 | | 11/2001 |
| JP | 2004-301520 | | 3/2003 |
| JP | 2006-317325 | | 11/2006 |
| WO | WO 2005/121767 A1 | | 5/2005 |

OTHER PUBLICATIONS

International Search Report of PCT/JP2005/009402 mailed Nov. 8, 2005.

Japanese Office Action dated Jun. 19, 2008 regarding Japanese Patent Application No. 2006-078740, in Japanese with English translation.

Supplementary European Search Report of PCT/JP2007/055382 mailed Jun. 7, 2010.

Jane Hodgkinson et al., "Photothermal Detection of Trace Optical Absorption in Water by Use of Visible-Light-Emitting Diodes", Applied Optics, vol. 37, No. 31 (Nov. 1, 1998), pp. 7320-7326.

Jane Hodgkinson et al., "Photothermal Detection of Trace Compounds in Water, Using the Deflection of a Water Meniscus", Meas. Sci. Technol., vol. 9 (1998), pp. 1316-1323. IOP Publishing, Ltd.

* cited by examiner

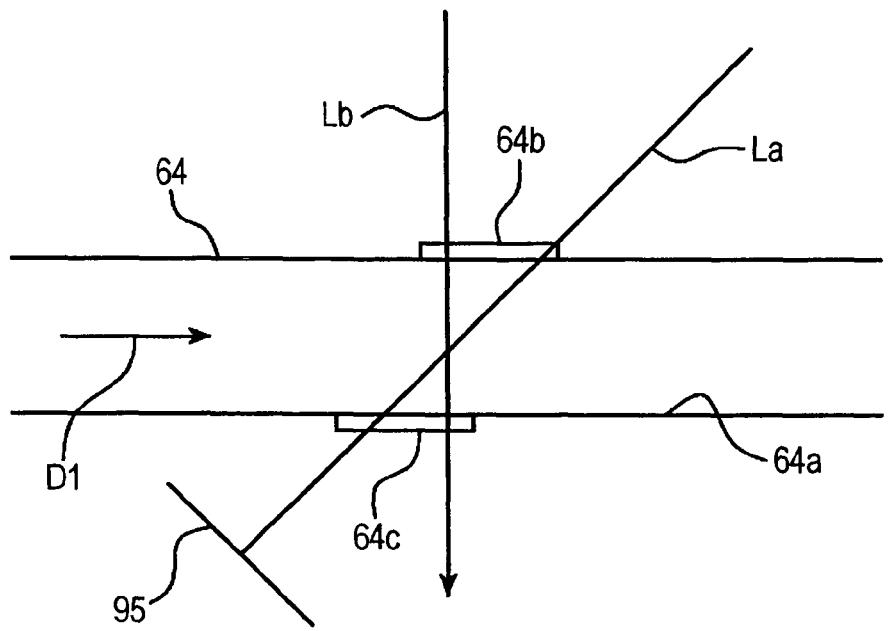
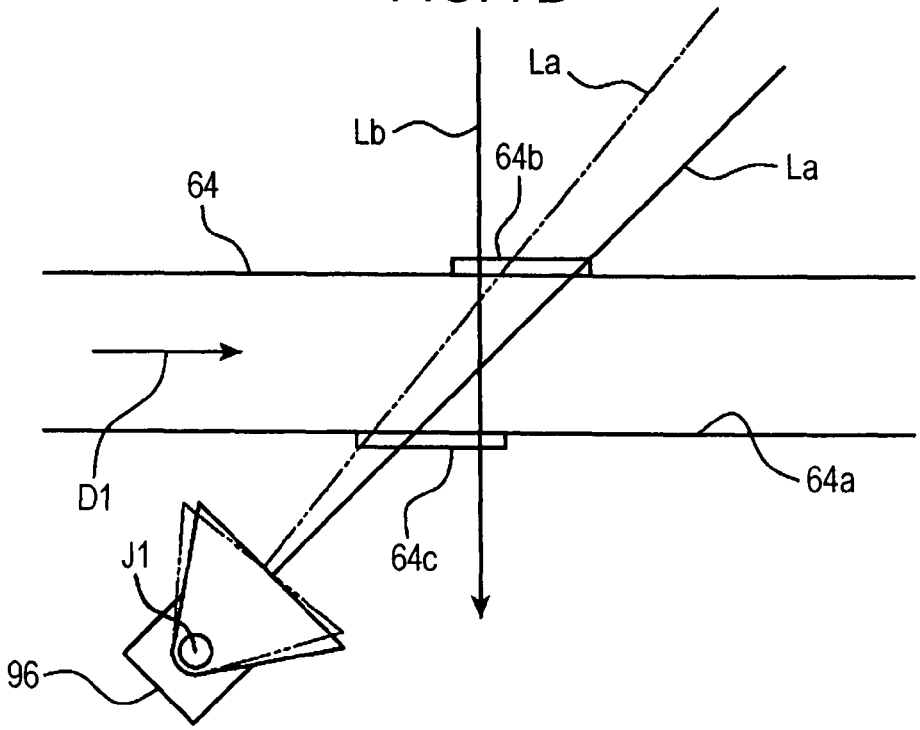

ANALYZER FOR ABSORPTION SPECTROMETRY OF IMPURITY CONCENTRATION CONTAINED IN LIQUID USING EXCITING LIGHT

TECHNICAL FIELD

The present invention relates to an analyzer for analyzing a specified component among components contained in a sample.

BACKGROUND ART

There have been known analyzers each including a detection portion for detecting a specified component in a sample.

This type of detectors includes a detector for detecting absorbance of a specified component (for example, a liquid chromatographic detector of Patent Document 1).

However, the detector of Patent Document 1 directly detects absorbance for analyzing a component and thus has difficulty in improving analytical precision.

Namely, in order to directly detect absorbance, an intensity ratio (transmittance) before and after transmission through a sample is required, and thus it is necessary to set a long optical path for light transmitted through the sample so that an intensity ratio to be detected is increased for improving analytical precision.

In order to extend the optical path, it is necessary to increase the sectional area of a passage of the sample or change the irradiation direction of light with respect to the flow passage. However, such a change in design becomes a large scale and is restricted by limitations on the space in an apparatus and the like.

Patent Document 1: Japanese Unexamined Patent Application Publication No. 2003-149135

DISCLOSURE OF INVENTION

The present invention has been achieved in consideration of the above-mentioned problem, and an object is to provide an analyzer capable of easily improving analytical precision.

As means for resolving the problem, the present invention relates to an apparatus for measuring impurities contained in a liquid flowing through a predetermined line, the apparatus including a sampling portion which is branched from the line and to which part of the liquid flowing through the line is introduced, an exciting light irradiation system for irradiating the liquid introduced into the sampling portion with exciting light, a measuring light irradiation system for irradiating, with measuring light different from the exciting light, a measurement object region where a photothermal effect of the impurities is produced by irradiation of the liquid with the exciting light, a phase change detector for detecting a phase change of the measuring light transmitted through the measurement object region, and a signal processor for outputting a measurement signal about the impurity concentration in the liquid on the basis of a detection signal from the phase change detector.

In the apparatus, part of the liquid flowing through the predetermined ling is introduced into the sampling portion and irradiated with the exciting light. The exciting light allows the impurities in the liquid to produce a photothermal effect. The measurement object region which exhibits the photothermal effect is irradiated with the measuring light different from the exciting light, and the refractive index of the measuring light is changed by the photothermal effect.

The change in refractive index changes the phase of the measuring light so that the degree of the photothermal effect, i.e., the absorbance of the exciting light, can be determined on the basis of the detection result of the phase change of the measuring light. Consequently, the weight of the impurities contained in the liquid and the concentration in the liquid can be measured.

Therefore, the apparatus is capable of efficiently analyzing the impurity concentration in the liquid with high precision. Further, the apparatus is capable of analyzing the impurities online without stopping the passage of the liquid through the line.

Further, the present invention provides an analyzer for analyzing a component to be analyzed which is separated from a sample containing a plurality of components, the analyzer including a separation portion having a passage formed therein, a separation purification portion capable of passing the components in the passage with differences in speed, and a detection portion for irradiating the sample in the passage with exciting light having the absorption wavelength of the component to be analyzed and for irradiating the irradiated region with measuring light having a wavelength other than the absorption wavelength of the component to be analyzed to detect a phase change of the measuring light before and after transmission through the sample.

According to the present invention, the component to be analyzed is exited by irradiation with the exciting light to cause photothermal conversion, and a temperature change in the sample which generates heat due to the photothermal conversion is measured as a change in refractive index of the sample on the basis of the measuring light before and after the transmission through the sample, thereby permitting quantitative analysis of the component to be analyzed.

Namely, the analyzer according to the present invention is capable of improving analytical precision by increasing the degree of the photothermal conversion, and thus even when the concentration of the component to be analyzed is low, high-precision analysis can be performed by increasing the intensity of the exciting light which induces the photothermal conversion.

Therefore, according to the present invention, analytical precision can be easily improved by a relatively simple method such as a method of increasing the intensity of exciting light.

BRIEF DESCRIPTION OF DRAWINGS

FIG. 7A is an enlarged side view showing a portion of a separation/purification analyzer provided with a mirror according to another embodiment of the present invention, and FIG. 7B is an enlarged side view showing a portion of a separation/purification analyzer provided with a an optical axis control portion according to still another embodiment of the present invention.

BEST MODE FOR CARRYING OUT THE INVENTION

A first embodiment of the present invention will be described with reference to FIGS. 1 and 2.

Figure 1:
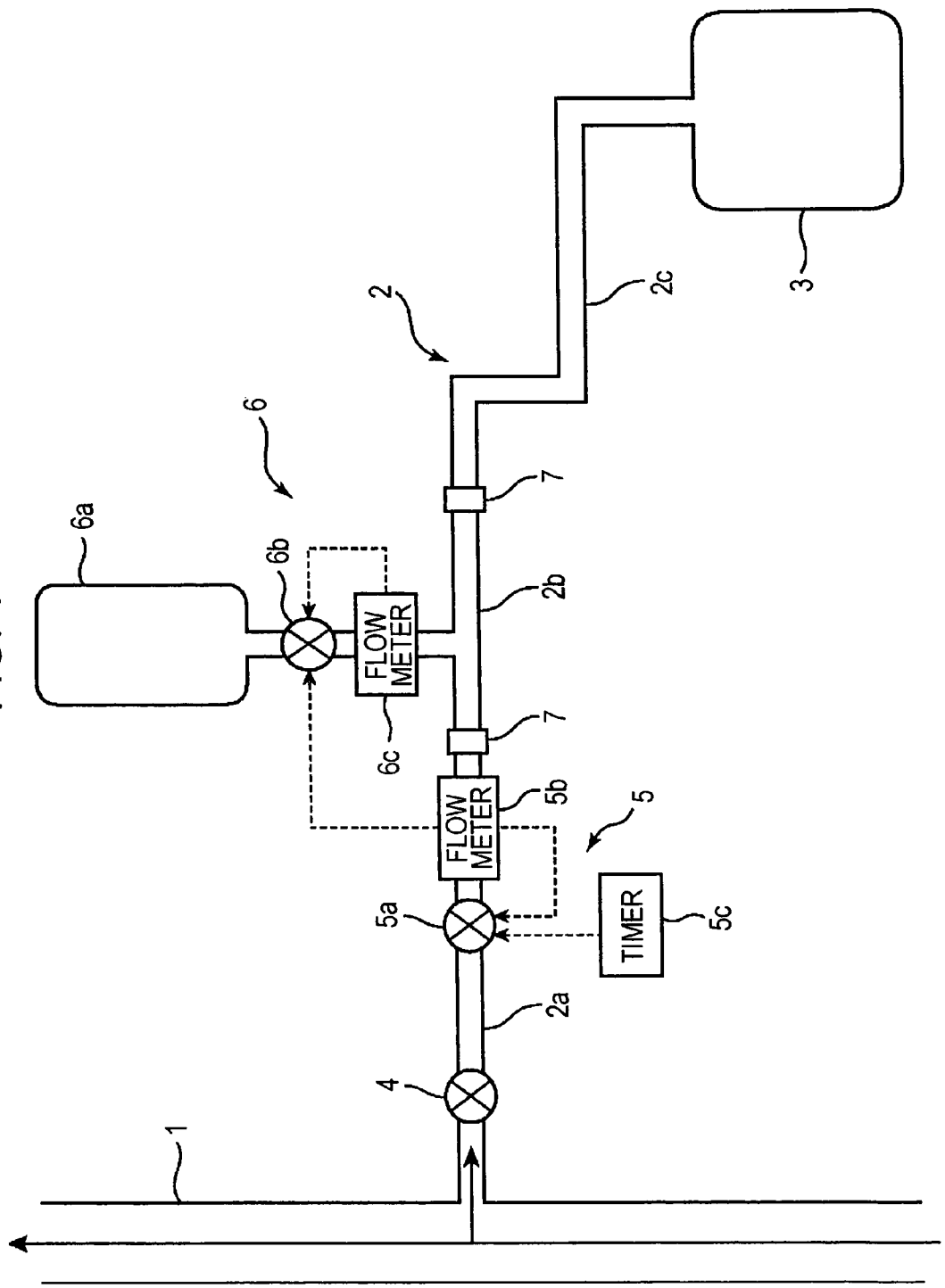
FIG. 1 is a drawing showing the entire configuration of an impurity analyzer according to a first embodiment of the present invention.

FIG. 1 shows the entire configuration of an impurity analyzer according to this embodiment. The analyzer is adapted to analyze impurities contained in a liquid (e.g., ultrapure water or process water) flowing through a predetermined line 1 and includes a branch line 2 branched from the line 1 and a tank 3 connected to the end of the branch line 2. The branch line 2 has an inlet portion 2a, a coloring portion 2b, and an absorption spectrometric portion 2c in that order from the upstream side.

The inlet portion 2a is provided with a main valve 4 and a flow rate control portion 5. The main valve 4 is opened and closed for switching on and off introduction of the liquid into the branch line 2. The flow control portion 5 is adapted to control the flow rate of the liquid flowing through the branch line 2.

Specifically, the flow control portion 5 is provided with a valve device 5a including an electric control portion, a flow meter 5b, and a timer 5c. The flow meter 5b measures the flow rate of the liquid downstream of the valve device 5a. The timer 5c inputs a command signal periodically to the valve device 5a for a predetermined time (for example, only 1 minute per hour) at a predetermined time interval. The valve device 5a is opened only when receiving the command signal from the timer 5c and, at the same time, calculates a target degree of opening on the basis of a measurement signal from the flow meter 5b and is opened in the target degree of opening. The target opening degree is calculated so that the liquid flow rate measured by the flow meter 5b is brought near to a predetermined target flow rate.

A reagent addition portion 6 is connected to the coloring portion 2b. In the reagent addition portion 6, a reagent is added to the liquid in the coloring portion 2b in order to permit analysis when the impurities contain a metal or metal ions not having light absorption properties. The reagent used produces a complex which absorbs light at a specified wavelength by chemical reaction with the impurities composed of the metal or metal ions.

The reagent addition portion 6 has a reagent tank 6a in which the reagent is stored, a valve device 6b including an electric control portion, and a flow meter 6c. The valve device 6b is interposed between the reagent tank 6a and the coloring portion 2b, for controlling the flow rate of the reagent supplied to the coloring portion 2b from the reagent tank 6a. The flow meter 6c measures the reagent flow rate downstream of the valve device 6b. The valve device 6b calculates a target flow rate of the reagent added on the basis of the liquid flow rate measured by the flow meter 5b and further calculates a target opening degree for bringing the flow rate of the reagent added, which is measured by the flow meter 6c, near to the target flow rate of the reagent added so that the valve device 6b is opened in the target opening degree.

The coloring portion 2b and the reagent addition portion 6 can be appropriately omitted depending on the type of impurities. For example, when impurities to be analyzed are composed of only organic molecules having absorption in an ultraviolet region, a coloring operation is not particularly required. The type of the reagent used is also appropriately selected according to the type of impurities. For example, when the impurity is Fe(II), a nitrosophenol reagent is suitable as the reagent. The nitrosophenol reagent produces complex ions having an absorption wavelength region of 700 to 800 nm by a reaction with the Fe(II).

Check valves 7 are provided upstream and downstream of the coloring portion 2b. In other words, a portion held between both check valves 7 corresponds to the coloring portion 2b. The upstream check valve 7 prevents the liquid and the reagent in the coloring portion 2b from flowing back to the inlet portion 2a side, and the downstream check valve 7 prevents the liquid in the absorption spectrometric portion 2c, which will be described below, from flowing back to the coloring portion 2b side.

The absorption spectrometric portion 2c is provided downstream of the coloring portion 2b, and in an example shown in FIG. 1, it includes a linear pipe portion. As shown in FIG. 2, a specified region of the pipe wall of the absorption spectrometric portion 2c is configured to have an optical incidence window 8A and emission window 8B which are composed of a material having the property of transmitting exciting light Le and measuring light Lm, which will be described below. In addition, an absorption spectrometric equipment is disposed near the absorption spectrometric portion 2c. This equipment includes an exciting light irradiation system 10, a measuring light irradiation system 20, a photodetector 36, and a signal processor 40.

Figure 2:
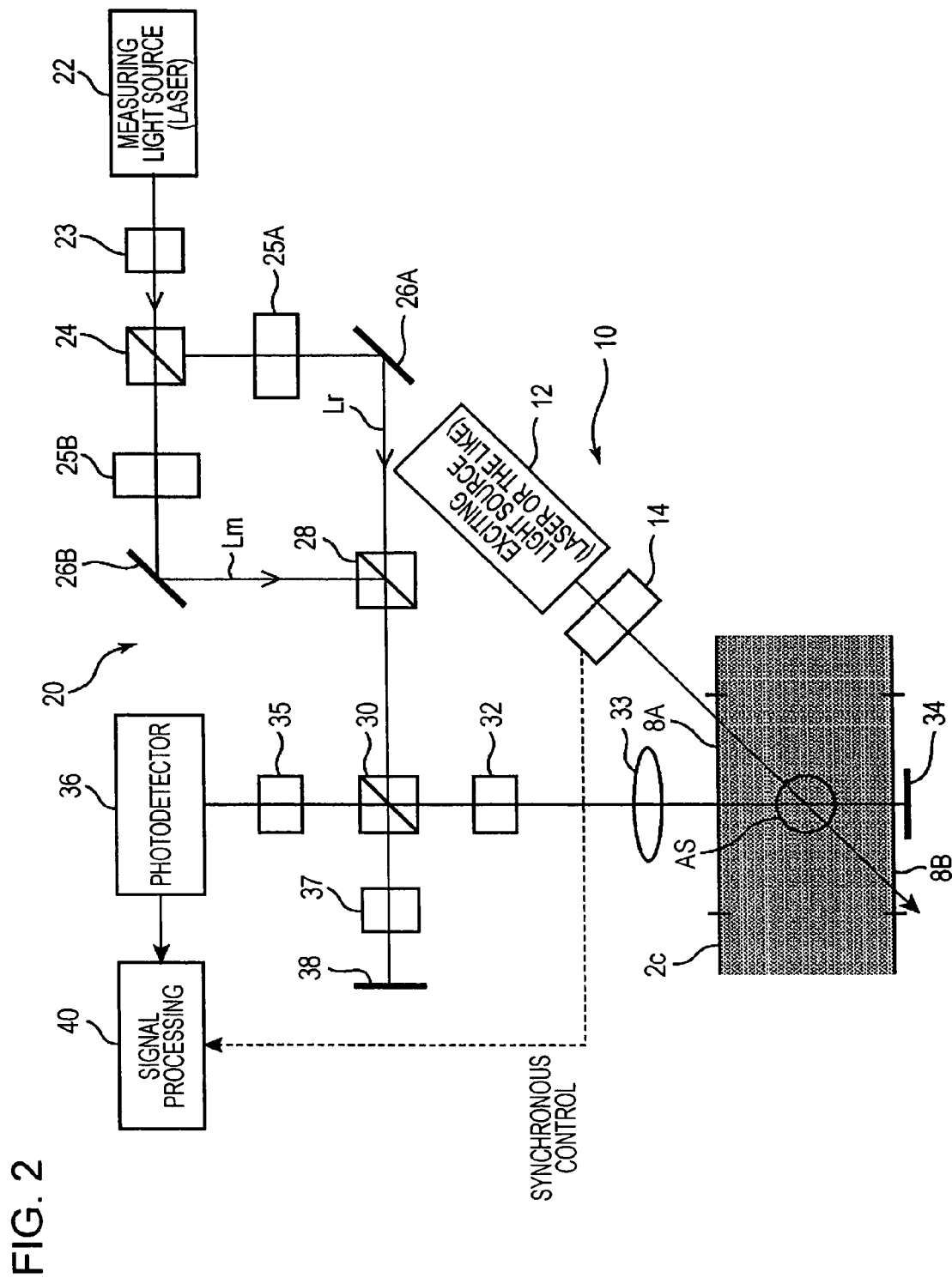
FIG. 2 is a drawing showing an absorption spectrometric portion of the impurity analyzer.

The exciting light irradiation system 10 is provided with an exciting light source 12 and a modulation mechanism 14, for irradiating the Liquid flowing through the absorption spectrometric portion 2c with the exciting light Le from the incidence window 8A in a specified direction (in the example shown in FIG. 2, an oblique direction).

As the exciting light source 12, for example, a xenon lamp which emits white light or a mercury lamp which emits ultraviolet light is preferably used. The wavelength is selected so that it can be absorbed by the impurities or the complex produced in the coloring portion 2b. Light emitted from the exciting light source 12 is separated into parts by a spectroscopic mechanism not shown and is incident on the modulation mechanism 14. The modulation mechanism 14 includes, for example, a chopper, for periodically modulating the intensity of the light to produce the exciting light Le suitable for absorption spectrometry described below.

The measuring light irradiation system 20 is adapted to irradiate a measurement object region AS in which a photoelectric effect is produced due to absorption of the exciting light Le by the impurities or the complex, with the measuring light Lm for measuring a change in refractive index due to the photoelectric effect.

The measuring light irradiation system 20 has a measuring light source 22. As the measuring light source 22, for example, a He—Ne laser generator with an output of 1 mW is used. Light emitted from the measuring light source 22 first passes through a λ/2 wavelength plate 23 which controls the polarization plane of the light. After the control, the light is incident on a polarized beam splitter 24. The polarized beam splitter 24 separates the light into two polarized lights perpendicular to each other, specifically reference light Lr and the measuring light Lm.

The reference light Lr is shifted in frequency (converted in frequency) by an acoustooptic modulator 25A, reflected by a mirror 26A, and input to a polarized beam splitter 28. The measuring light Lm is shifted in frequency (converted in frequency) by an acoustooptic modulator 25B, reflected by a mirror 26B, and input to the polarized beam splitter 28. The splitter 28 combines the reference light Lr and the measuring light Lm, and synthesized light is introduced into a polarized beam splitter 30.

The polarized beam splitter 30 reflects by 90° the measuring light Lm to the absorption spectrometric portion 2c but transmits the reference light Lr. The reference light Lr passes through a ¼ wavelength plate 37, is reflected by 180° with a mirror 38, again passes through the ¼ wavelength plate 37, and then returns to the polarized beam splitter 30. In this case, the ¼ wavelength plate 37 rotates by a total of 90° the polarization plane of the reference light Lr. Therefore, the reference light Lr is reflected by 90° with the polarized beam splitter 30 to the side opposite to the absorption spectrometric portion 2c. Then, the reference light Lr passes through a polarizing plate 35 and is input to the photodetector 36.

The measuring light Lm reflected by 90° with the polarized beam splitter 30 passes through a ¼ wavelength plate 32, a condensing lens 33, and the incidence window 8A of the absorption spectrometric portion 2c and is then incident on the measurement object region AS. The measuring light Lm passes through the measurement object region AS and through the emission window 8B at the back thereof, is reflected by 180° with a mirror 34, again passes through the measurement object region AS and the ¼ wavelength plate 32, and returns to the polarized beam splitter 30. In this case, the measuring light Lm reciprocates through the ¼ wavelength plate 32, and thus the polarization plane of the measuring light Lm is rotated by 90°. The measuring light Lm subjected to the operation of rotating the polarization plane passes through the polarized beam splitter 30, combines with the reference light Lr, and then travels toward the polarizing plate 35 and the photodetector 36.

Each of the incidence window 8A and the emission window 8B is made of a material with a size which allows transmission of each of the lights. The material is preferably, for example, quartz or PDMS (polydimethylsiloxane).

The reference light Lr and the measuring light Lm interfere with each other in the polarizing plate 35, and the intensity of interference light is converted to an electric signal (detection signal) by the photodetector 36. Namely, the measuring light irradiation system 20 includes a spectroscopic optical system for separating the measuring light Lm emitted from the measuring light source 22 into the measuring light Lm and the reference light Lr and for allowing the reference light Lr to interfere with the measuring light Lm transmitted through the measurement object region AS. The spectroscopic optical system and the photodetector 36 constitute a phase change detector.

The detection signal of the photodetector 36 is input to the signal processor 40. The signal processor 40 takes in the detection signal with timing synchronizing with the period of the modulation operation of the modulation mechanism 14. In other words, sampling is periodically carried out.

On the basis of the sampled detection signal, the signal processor 40 calculates a change in phase of the measuring light Lm, i.e., a change in phase due to transmission of the measuring light Lm through the liquid. Further, the signal processor 40 forms data about changes with time of the phase change and automatically calculates a change in refractive index and further calculates the impurity concentration in the liquid on the basis of the data as described below. The principle is as follows:

The intensity S1 of the interference light is represented by the following expression (1):

$$S1 = C1 + C2 \cdot \cos(2\pi \cdot fb \cdot t + \phi) \quad (1)$$

In the expression, C1 and C2 are each a constant determined by the optical systems such as the polarized beam splitter and the transmittance of the liquid, $\phi$ is a phase difference due to a difference between the optical path lengths of the reference light Lr and the measuring light Lm, and fb is a frequency difference between the reference light Lr and the measuring light Lm. The expression (1) indicates that a change in the phase difference $\phi$ is determined by a change in the interference light intensity S1 (i.e., a difference between the intensity without irradiation with the exciting light Le or lower intensity and higher intensity).

When the intensity of the exciting light Le is periodically modulated at a frequency f by the modulation operation (e.g., rotation of a chopper) of the modulation mechanism 14, each of the refractive index of the liquid and the optical path length of the measuring light Lm is changed at the frequency f. On the other hand, the optical path length of the exciting light Le is constant, and thus the phase difference $\phi$ is also changed at the frequency f. Therefore, when the timing of sampling of the detection signal is synchronized with the modulation operation in order to measure (calculate) a change in the phase difference $\phi$ with respect to a component of the frequency f (a component with the same period as the intensity modulation period of the exciting signal), it is possible to measure only a change in refractive index of the liquid while removing the influence of a noise not having the component of the frequency f. The measurement improves the S/N ratio of measurement of the phase difference $\phi$.

When the exciting light source 12 is a laser diode or LED, the modulation can also be made by controlling a power supply of the exciting light source 12 using an electric circuit.

Figure 3:
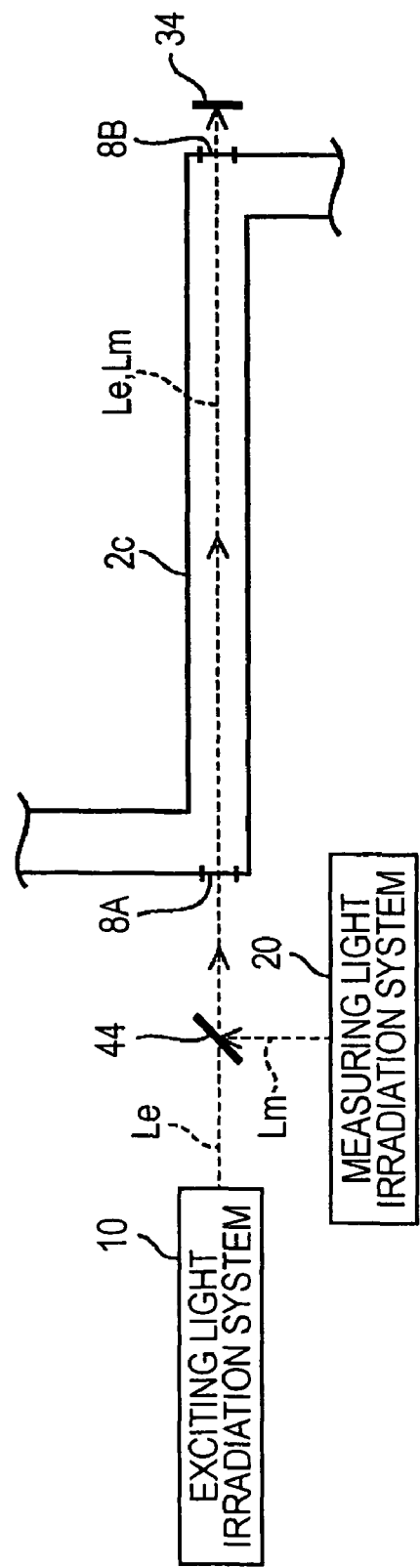
FIG. 3 is a drawing showing an example in which exciting light and irradiating light are coaxially applied in the impurity analyzer.

In addition, the direction of the optical axis of the exciting light Le can be appropriately set. For example, as shown in FIG. 3, the exciting light Le and the measuring light Lm can be coaxially applied along the flow direction of the liquid in the absorption spectrometric portion 2c using a dichroic mirror 44. The dichroic mirror 44 has the property of directly transmitting the exciting light Le and reflecting by 90° the measuring light Lm. The property can make both the light Le and the light Lm coaxial when the emission directions of the exciting light Le and the measuring light Lm from the irradiation systems 10 and 20, respectively, are 90° different from each other. The coaxial irradiation enables irradiation along the flow direction of the liquid. The irradiation can increase the measurement optical path length (the length of the measurement object region AS) in the absorption spectrometric portion 2c, thereby improving analytical precision. In order to perform the irradiation, the incidence-side optical window 8A is provided at one of the upstream end and the downstream end of the absorption spectrometric portion 2c, and the emission-side optical window 8B is provided at the other end.

Next, an impurity analysis method carried out in the impurity analyzer shown in FIGS. 1 and 2 is described.

In FIG. 1, when the main valve 4 is opened, part of the liquid flowing in the line 1 flows into the branch line 2. The valve opening may be performed manually or using an automatic switching device interlocking with on/off of a switch.

The flow rate of the liquid flowing into the branch line 2 is controlled by the flow control portion 5. Specifically, the valve device 5a of the flow control portion 5 allows the liquid to periodically pass for a predetermined time on the basis of the command signal of the timer 5c and controls the flow rate of the liquid to the target flow rate. The control stabilizes the flow rate of the liquid in the coloring portion 2b and the absorption spectrometric portion 2c on the downstream side.

In the coloring portion 2b, a reagent is added from the reagent addition portion 6 to the liquid flowing in the coloring portion 2b. The flow rate of the reagent added is controlled to be appropriate for the flow rate of the liquid by the operation of the valve device 6b. The reagent is mixed with the liquid in the coloring portion 2b to produce a complex suitable for absorption spectrometry, i.e., a complex absorbing light at a specified wavelength, by a chemical reaction with a metal or metal ions as impurities in the liquid. The production of the complex enables absorption spectrometry even when the impurities contain a metal or metal ions.

Although, in this embodiment, the reagent is added to the liquid flowing in the coloring portion 2b, the liquid may be stored in a stationary state in the coloring portion according to the present invention. The coloring operation in a stationary state can be realized by, for example, closing on-off valves used as the check values 7. In this case, the on-off values are closed only for a predetermined reaction time after the addition of the reagent. After the passage of the reaction time, the on-off value on the downstream side is opened to introduce the liquid containing the complex produced by adding the reagent into the subsequent absorption spectrometric portion 2c. As means for promoting the reaction, it is effective to control the temperature of the reaction region using a heater or the like or to promote mixing of the liquid and the reagent by rotation with a stirring blade.

In the absorption spectrometric portion 2c, the liquid flowing in the absorption spectrometric portion 2c is irradiated with the exciting light Le from the exciting light irradiation system 10 shown in FIG. 2. The wavelength of the exciting light Le is one which can be absorbed by the complex. Therefore, the exciting light Le is absorbed in a degree corresponding to the amount of the complex in the liquid. Namely, the complex absorbs the exciting light Le and a photothermal effect is exhibited due to the absorption.

On the other hand, the measurement object region AS in which the photothermal effect is produced is irradiated with the measuring light Lm from the measuring light irradiation system 20. The measuring light Lm passes through the measurement object region AS, is reflected upward by the mirror 34, and again passes through the measurement object region AS. In the measurement object region AS, the refractive index is changed according to the amount of heat generated by the photothermal effect, and the phase difference φ is changed according to the refractive index. Therefore, the intensity of interference light of the measuring light Lm returning to the measuring light irradiation system 20 and the reference light Lr in the measuring light irradiation system 20 is changed according to the amount of heat generated by the photothermal effect. Further, a detection signal corresponding to the intensity of interference light is generated from the photodetector 36 in the measuring light irradiation system 20 and input to the signal processor 40.

The signal processor 40 takes in the detection signal at a sampling period synchronizing with the modulation operation of the modulation mechanism 14. On the basis of the detection signal, a change in the refractive index of the liquid due to the photothermal effect is calculated. The change in the refractive index corresponds to the absorbance of the complex contained in the liquid, and consequently corresponds to the amount of original impurities. Therefore, the weight of impurities contained per unit volume of liquid (solvent), i.e., the impurity concentration, can be calculated on the basis of the change in the refractive index, the flow rate of the liquid, and the flow rate of the reagent added. The signal processor 40 forms a measurement signal about the impurity concentration and outputs the signal to a display device or storage device not shown, or a warning device for an operator according to demand.

The detection signal can be converted to the impurity weight by, for example, using a calibration curve which is previously prepared. The calibration curve can be formed by performing the absorption spectrometry for samples each having known absorbance and concentration and examining a relation between measurement signals and the absorbance.

In the apparatus, each of the refractive index of the liquid and the optical path length of the detection signal thereof is changed with the same period as the intensity modulation of the exciting light Le. Therefore, when the detection signal is taken in the signal processor 40 with timing synchronizing with the period, it is possible to measure only a change in refractive index of the liquid while removing the influence of a noise not having a frequency component of the exciting light. This improves the S/N ratio of measurement of the phase change.

In the above-described impurity analysis method, part of the liquid flowing in the line 1 is introduced into the branch line 2 constituting the sampling portion, and the introduced liquid is irradiated with the exciting light Le and the measuring light Lm. Therefore, the analysis can be performed on line with high precision without stopping the line 1. In addition, unlike in a conventional method using a surface analyzer, a high degree of concentration is not particularly required as a pre-treatment, and thus the analysis can be efficiently achieved by a sample configuration.

In particular, the method including irradiating the liquid flowing through the branch line 2 with the light Le and the light Lm and adding the reagent thereto permits continuous real-time analysis. The continuous analysis cannot be realized by a conventional known method, i.e., a method requiring a concentration treatment (i.e., batch treatment) with a porous membrane.

However, this does not means that the present invention does not include an embodiment in which the liquid branched from the line 1 is stored and undergoes the absorption spectrometry and coloring treatment in a stationary state.

Further, the present invention includes an embodiment in which the liquid is concentrated before irradiation with the exciting light and the measuring light. Even when the concentration is performed, unlike in a conventional method using a surface analyzer, a simple treatment is sufficient for the concentration. In addition, the concentration treatment further improves the analytical precision.

Figure 4:
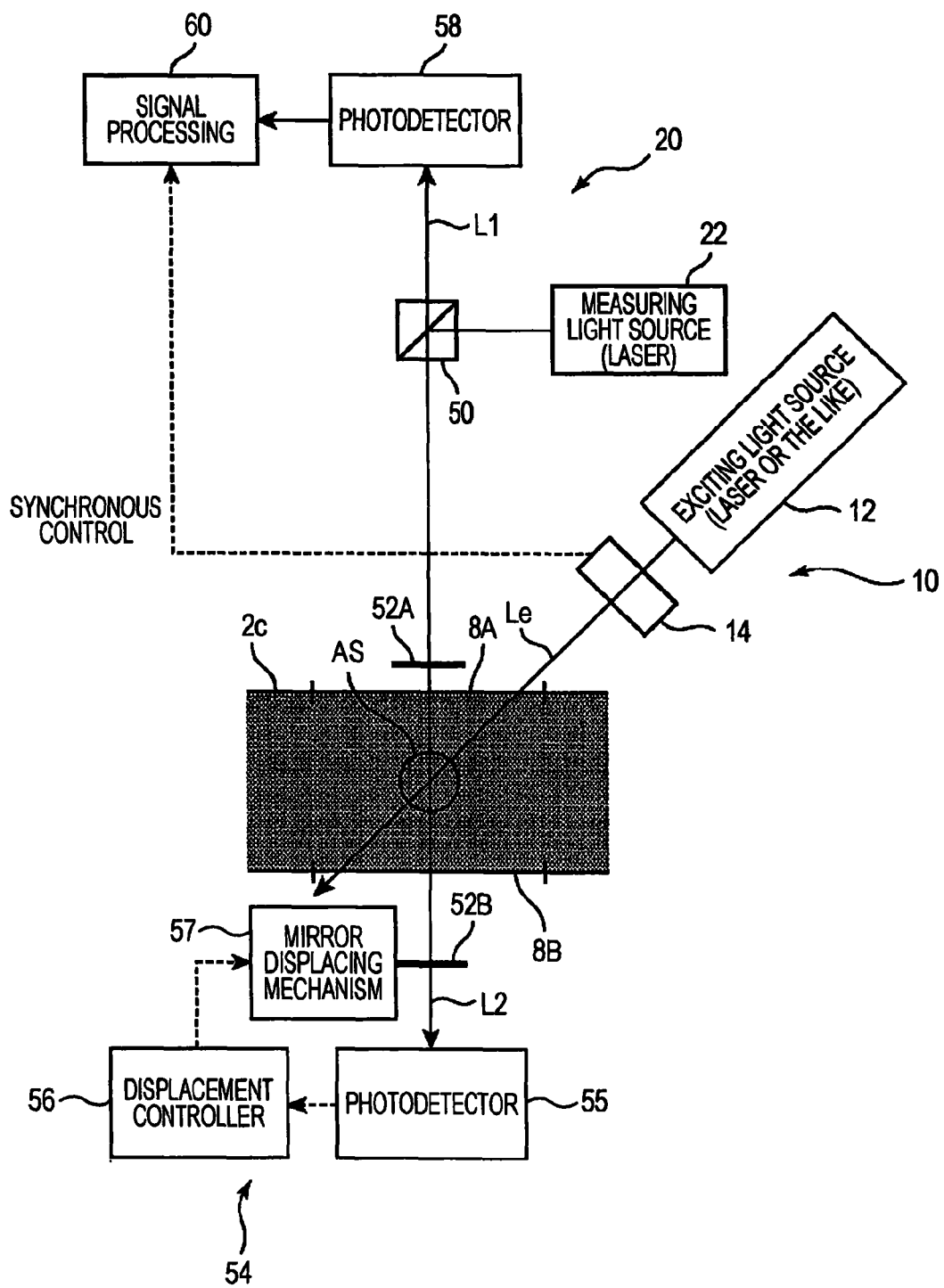
FIG. 4 is a drawing showing an absorption spectrometric portion of an impurity analyzer according to a second embodiment of the present invention.

Next, an absorption spectrometric equipment of an impurity analyzer according to a second embodiment will be described on the basis of FIG. 4. In FIG. 4, the same components as that shown in FIG. 2 are denoted by the same reference numerals, and description thereof is omitted.

In the second embodiment, the configuration of the exciting light irradiation system 10 is the same as that of the first embodiment. On the other hand, the measuring light irradiation system 40 is provided with a beam splitter 50, a pair of high-reflection mirrors 52A and 52B serving as reflecting portions, and a distance control mechanism 54 besides the measuring light source 22.

The high-reflection mirrors 52A and 52B are opposed to each other with the measurement object region AS, on which the exciting light Le is incident, provided therebetween. Each of the high-reflection mirrors 52A and 52B has the property of reflecting most of the incident light (measuring light Lm) and transmitting only a portion of the light.

The distance control mechanism 54 is adapted to automatically control the distance between both high-reflection mirrors 52A and 52B and is provided with a photodetector 55, a displacement controller 56, and a mirror displacing mechanism 57.

The mirror displacing mechanism 57 displaces the high-reflection mirror 52B of the high-refection mirrors 52A and 52B in a direction in which both mirrors 52A and 52B approach and separate from each other according to a control signal input from the displacement controller 56. The photodetector 55 detects the intensity of the measuring light Lm transmitted through the high-reflection mirror 52B to the side opposite to the measurement object region AS. The displacement controller 56 forms the control signal for displacing the high-reflection mirror 52B in a direction of suppressing variation of a detection signal of the photodetector 55 (i.e., a direction of maintaining a resonant condition of light reciprocating between the high-reflection mirrors 52A and 52B) on the basis of the detection signal of the photodetector 55 and inputs the control signal to the mirror displacing mechanism 57.

The control of the distance between both high-reflection mirrors 52A and 52B by the distance control mechanism 54 improves the measurement precision of the phase change by maintaining the resonant condition.

The principle of measurement by the above-described absorption spectrometric portion is as follows:

The light (measuring light Lm) emitted from the measuring light source 22 is reflected by 90° with the beam splitter 50 and reaches the high-reflection mirror 52A. The high-reflection mirror 52A reflects most of the measuring light Lm but allows transmission of a small portion thereof. The transmitted portion of the measuring light Lm passes through the measurement object region AS and is incident on the opposite high-reflection mirror 52B. Like the high-reflection mirror 52A, the high-reflection mirror 52B reflects most of the incident measuring light Lm but transmits a small portion thereof.

Therefore, a portion of the measuring light Lm is multiple-reflected between the high-reflection mirrors 52A and 52B while being repeatedly transmitted through the measurement object region AS, and a small portion of the measuring light Lm leaks outward from both high-reflection mirrors 52A and 52B at each time of reflection. The light transmitted through the high-reflection mirror 52A to the side opposite to the measurement object region AS results from superposition of lights having different numbers of times of reciprocation between the mirrors 52A and 52B. The light becomes reflection-side measuring light L1 by superposition of light reflected by the high-reflection mirror 52A to the beam splitter 50 side. Then, the light passes through the beam splitter 50 and is input to the photodetector 58.

The photodetector 58 inputs a detection signal corresponding to the intensity of the input reflection-side measuring light L1 to a signal processor 60. Like the signal processor 40 according to the first embodiment, the signal processor 60 takes in the detection signal with timing synchronizing with the modulation operation of the modulation mechanism 14 and calculates a change in phase of the measuring light Lm and an impurity concentration from a change in reflective index on the basis of the detection signal.

The specific calculation principle is as follows: As described above, the reflection-side measuring light L1 results from superposition of measuring lights having different numbers of times of reciprocation between the high-reflection mirrors 52A and 52B. Therefore, when the optical path length L between the mirrors coincides with $n \cdot \lambda/2$ (wherein n is a positive integer, and $\lambda$ is the wavelength of the measuring light between the two mirrors), the phases of the multiple-reflected measuring lights are synchronized and emphasized by each other (i.e., resonated) to produce the maximum intensity P2max of light intensity P2. However, when the optical path length L between the mirrors deviates from $n \cdot \lambda/2$, the multiple-reflected measuring light having a larger number of times of reciprocation between the mirrors is significantly shifted in phase, resulting in a large decrease in intensity of transmission-side measuring light L2 even when the optical path length L is slightly changed.

When the reflectance of each of the high-reflection mirrors 52A and 52B is R (R=0 to 1) and the optical path length between the mirrors satisfying the relation $L=n \cdot \lambda/2$ is Ln ($=n \cdot \lambda/2$), a range $\Delta L$ of optical path lengths (hereinafter, referred to as "the optical path length range") which cause a change in the intensity P2 of the transmission-side measuring light L2 with the optical path length Ln between the mirrors as a center is represented by the following expression (2):

$$\Delta L = Ln/F$$

$$\text{wherein } F = \pi \cdot \sqrt{R}/(1-R) \tag{2}$$

The expression (2) indicates that as the reflectance R of each of the high-reflection mirrors 52A and 52B increases and the optical path length Ln between the mirrors decreases, a slight change in the optical path length can be measured with high sensitivity by decreasing the optical path length range $\Delta L$.

On the other hand, according to the energy conservation law, the intensity P1 of the reflection-side measuring light L1 becomes equal or close to ($\approx$P1max−P2) an intensity obtained by subtracting the intensity P2 of the transmission-side measuring light L2 from intensity P1max which is substantially equal to the initial intensity of the measuring light.

The analysis according to this embodiment is carried out using the above-mentioned principle, for example, according to the procedures below.

Step 1: The initial distance between the high-reflection mirrors 52A and 52B is controlled. Specifically, first, multiple reflection is carried out between the high-reflection mirrors 52A and 52B without irradiation with the exciting light Le, and the intensity P1 of the reflection-side measuring light L1 is detected by the photodetector 58. Then, the initial distance between the high-reflection mirrors 52A and 52B is controlled so that the detected intensity P1 coincides with the minimum intensity P1min ($\approx$P1max−P2max) or an intermediate intensity between the minimum intensity and the maximum intensity P1max.

The distance may be controlled so that the detected intensity P2 of the transmission-side photodetector 55 coincides with the maximum intensity P2max or an intermediate intensity between the minimum intensity and the maximum intensity P2max. In this case, when the intensity P2 (signal) detected by the photodetector 55 is changed (the intensity P1 detected by the photodetector 58 is also changed), the high-reflection mirror 52B is automatically displaced in an amount corresponding to the change by the displacement control mechanism 56 and the mirror displacing mechanism 57. In other words, the distance between the high-reflection mirrors 52A and 52B is controlled in a direction of suppressing variation in the detection signal of the photodetector 55. Then, during the measurement, the position of the high-reflection mirror 57 is continuously controlled by the displacement control mechanism 56 and the mirror displacing mechanism 57.

Step 2: The liquid is intermittently irradiated with the exciting light Le with intensity modulated by the modulation mechanism 14 while the positions of the high-reflection mirrors 52A and 52B are controlled. As a result, the exciting light Le allows the impurities contained in the liquid to produce the photothermal effect which changes the refractive index of the liquid. The change in the refractive index causes a change in the optical path length L between the mirrors. This change significantly changes the detection signal (detection signal of intensity of the reflection-side measuring light L1) input to the signal processor 60 from the photodetector 58. The detection signal is stored in a storage portion in the signal processor 60.

Step 3: The signal processor 60 measures a change in refractive index on the basis of the detection signal. The measurement is carried out by, for example, using a data table or conversion equation (data table or conversion equation showing a corresponding relation between the detection signal and change in refractive index) which is previously prepared. On the basis of the change in refractive index, the impurity concentration in the liquid is analyzed with high precision.

The measurement can also be carried out on the basis of the intensity P2 of the transmission-side measuring light L2 detected by the photodetector 55. This is because the total of the intensity P2 and the intensity P1 of the reflection-side measuring light L1 is constant ($\neq$P1max).

In the present invention, the optical systems can be arranged in any one of various forms. The arrangement may be any desired one as long as it permits the irradiation of the measurement object region AS with the measuring light and the detection of a change in phase of the measuring light.

Prior art relating to the first and second embodiments is described below.

When a liquid with extremely high purity, such as ultrapure water or process water, is used in industrial equipment such as a semiconductor factory, a power plant, or the like, it is important to control the purity of the liquid, i.e., monitor the impurity concentration.

As a conventional method for analyzing such an impurity concentration, there is known a method using absorption spectrometry as disclosed in Japanese Unexamined Patent application Publication No. 2001-153855. In this method, part of a liquid flowing in an ultrapure water or process water line is branched from the line and passed through a porous membrane so that the amount of impurities captured in a concentrated state by the porous membrane is measured by a surface analyzer.

Since the method described in Japanese Unexamined Patent application Publication No. 2001-153855 uses the surface analyzer, the porous membrane is required to have a high degree of concentration. Therefore, expensive equipment including the porous membrane is required. Further, the time required for the concentration and the operation of exchanging the porous membrane decrease the efficiency of analysis. In addition, the method has difficulty in significantly increasing the analytical precision.

On the other hand, it is required for the analysis of impurities to be carried out on line (i.e., without stopping the line of the ultrapure water or the like).

In consideration of the above-mentioned situation, each of the above-described embodiments is aimed at providing a method and apparatus capable of efficiently analyzing the concentration of impurities contained in ultrapure water or process water with high precision.

As means for resolving the problem, each of the embodiments relates to a method for measuring impurities contained in a liquid flowing through a predetermined line, the method including an operation of introducing part of the liquid flowing through the line into a sampling portion which is previously provided to be branched from the line, an operation of irradiating the liquid introduced into the sampling portion with exciting light at a wavelength appropriate for the absorption property of the impurities to be measured, an operation of irradiating, with measuring light different from the exciting light, a measurement object region where the photothermal effect of the impurities is produced by irradiation of the liquid with the exciting light, an operation of detecting a phase change of the measuring light transmitted through the measurement object region, and an operation of calculating the impurity concentration in the liquid on the basis of the result of detection.

Also, each of the embodiments relates to an apparatus for measuring impurities contained in a liquid flowing in a predetermined line, the apparatus including a sampling portion which is branched from the line and to which part of the liquid flowing through the line is introduced, an exciting light irradiation system for irradiating the liquid introduced into the sampling portion with exciting light, a measuring light irradiation system for irradiating, with measuring light different from the exciting light, a measurement object region where the photothermal effect of the impurities is produced by irradiation of the liquid with the exciting light, a phase change detector for detecting a phase change of the measuring light transmitted through the measurement object region, and a signal processor for outputting a measurement signal about the impurity concentration in the liquid on the basis of a detection signal from the phase change detector.

In the method and the apparatus, part of the liquid flowing through the predetermined ling is introduced into the sampling portion and irradiated with the exciting light. The exciting light allows the impurities in the liquid to produce the photothermal effect. The measurement object region which exhibits the photothermal effect is irradiated with the measuring light different from the exciting light, and the refractive index of the measuring light is changed by the photothermal effect. The change in refractive index changes the phase of the measuring light so that the degree of the photothermal effect, i.e., the absorbance of the exciting light, can be determined on the basis of the detection result of the phase change of the measuring light. Consequently, the weight of the impurities contained in the liquid and the impurity concentration in the liquid can be measured.

Therefore, unlike the above-described conventional technique, the method and apparatus do not require a high degree of concentration treatment and are capable of efficiently analyzing the impurity concentration in the liquid with high precision. Further, the impurities can be analyzed online without stopping the flow of the liquid through the line.

The gist of each of the embodiments includes a case in which the liquid is concentrated before irradiation with the exciting light and the measuring light. However, even when the concentration is performed, unlike in a conventional method using a surface analyzer, a simple treatment is sufficient for the concentration. In addition, the concentration treatment further improves the analytical precision.

When the impurities to be measured contain a metal or metal ions, the method more preferably includes an operation of mixing the liquid branched from the line with a regent which produces a complex absorbing light at a specified wavelength by a chemical reaction with the impurities before irradiation with the exciting light and then irradiating the liquid with light at a wavelength which can be absorbed by the complex as the exciting light. Therefore, even when the impurities contain a metal or metal ions, the analysis of the present invention can be performed.

The impurities composed of a metal or metal ions may have no light absorption property for wavelengths in all the ultra-violet region, the visible region, and the infrared region. In this case, the occurrence of the photothermal effect cannot be expected from the impurities as they are. However, since a complex having the property of absorbing the exciting light is produced by a chemical reaction between the impurities and the reagent added, light absorption and the photothermal effect of the complex can be achieved. By using the photo-thermal effect, the impurity concentration can be measured.

In the method according to each of the embodiments, the liquid branched from the line is passed at a predetermined flow rate through the specified portion of the sampling portion, and the liquid flowing through the specified portion is irradiated with the exciting light, thereby permitting the continuous real-time observation of the concentration of the impurities. In the method, the impurity concentration is calculated on the basis of the impurity weight in the liquid, which is determined from the detection result, and the flow rate of the liquid.

Even in such a case, the impurities containing a metal or metal ions can be analyzed using the reagent. Specifically, before the operation of irradiating with the exciting light, the reagent which produces a complex absorbing light at a specified wavelength by a chemical reaction with the impurities is added, at a flow rate corresponding to the flow rate of the liquid, to and mixed with the liquid flowing through the specified portion, followed by irradiation with light at a wavelength which can be absorbed by the complex as the exciting light. The impurity concentration in the liquid may be calculated on the basis of the weight of the impurities in the liquid, which is determined from the detection result, the flow rate of the liquid, and the flow rate of the reagent added.

On the other hand, when impurities containing a metal or metal ions are analyzed by the apparatus, the sampling portion may include the absorption spectrometric portion for irradiation with the exciting light and the measuring light and the coloring portion provided upstream of the absorption spectrometric portion, for adding and mixing the reagent to and with the liquid, the reagent producing a complex which absorbs light at a specified wavelength by a chemical reaction with the impurities. In the exciting light irradiation system, the liquid introduced from the coloring portion to the absorption spectrometric portion may be irradiated with light, as the exiting light, at a wavelength which can be absorbed by the complex.

In addition, the apparatus may include the sampling portion including a branch line connected to the line and a flow control portion for controlling the flow rate of the liquid flowing in the branch line to a specified flow rate. In the exciting light irradiation system, the liquid flowing through a specified portion of the branch line is irradiated with the exciting light. The signal processor calculates the impurity concentration in the liquid on the basis of the weight of the impurities in the liquid, which is determined from the detection result, and the flow rate of the liquid which is controlled by the flow control portion. In this case, the impurity concentration can be continuously observed in real time.

When impurities containing a metal or metal ions are analyzed by the apparatus, the branch line may include the absorption spectrometric portion for irradiating the liquid flowing in the branch line with the exciting light and the measuring light and the coloring portion provided upstream of the absorption spectrometric portion, and a reagent addition portion may be connected to the coloring portion, for adding and mixing the reagent to and with the liquid at a flow rate corresponding to the flow rate of the liquid, the reagent producing a complex which absorbs light at a specified wavelength by a chemical reaction with the impurities. In the exciting light irradiation system, the liquid flowing in the absorption spectrometric portion may be irradiated with light, as the exiting light, at a wavelength which can be absorbed by the complex. The signal processor may calculate the impurity concentration in the liquid on the basis of the weight of the impurities in the liquid, which is determined from the detection result, the flow rate of the liquid, and the flow rate of the reagent added.

The apparatus according to each of the embodiments, preferably, the exciting light irradiation system irradiates the sample with light at periodically modulated intensity as the exciting light, and the signal processor takes in the detection signal of the phase change detector with timing synchronizing with the period of the intensity modulation.

In the apparatus, since the detection signal changes synchronously with the period of the intensity modulation of the exciting light, the detection signal is taken in with timing synchronizing with the period. In this case, it is possible to measure only the phase change (i.e., the change in refractive index) while removing the influence of a noise not having a frequency component of the exciting light. This results in improvement in the S/N ratio of measurement of the phase change.

The phase change detector preferably includes a spectroscopic optical system for separating reference light from the measuring light and allowing the reference light to interfere with the measuring light transmitted through the measurement object region and a photodetector for detecting the intensity of the interference light. It is also preferred that the phase change detector includes light reflecting portions disposed opposite to each other on both sides of the measurement object region provided therebetween, and a photodetector. One of the light reflecting portions reflects part of the measuring light transmitted through the measurement object region toward the other reflecting portion to reciprocate the measuring light, and the photodetector receives the measuring light transmitted through at least one of the light reflecting portions toward the side opposite to the measurement object region and detects the intensity of the light. The apparatus can realize impurity analysis with high precision using multiple reflection of the measuring light between the light reflecting portions.

Further, the phase change detector of the latter analyzer more preferably includes a distance control mechanism for controlling the distance between the light reflecting portions in a direction of maintaining the resonant condition of light reciprocating between the light reflecting portions. The control of the distance between the light reflecting portions by the distance control mechanism maintains a resonant condition of light reciprocating between the light reflecting portions, thereby effectively enhancing the measurement precision of the phase change.

A third embodiment of the present invention will be described below with reference to FIG. 5.

Figure 5:
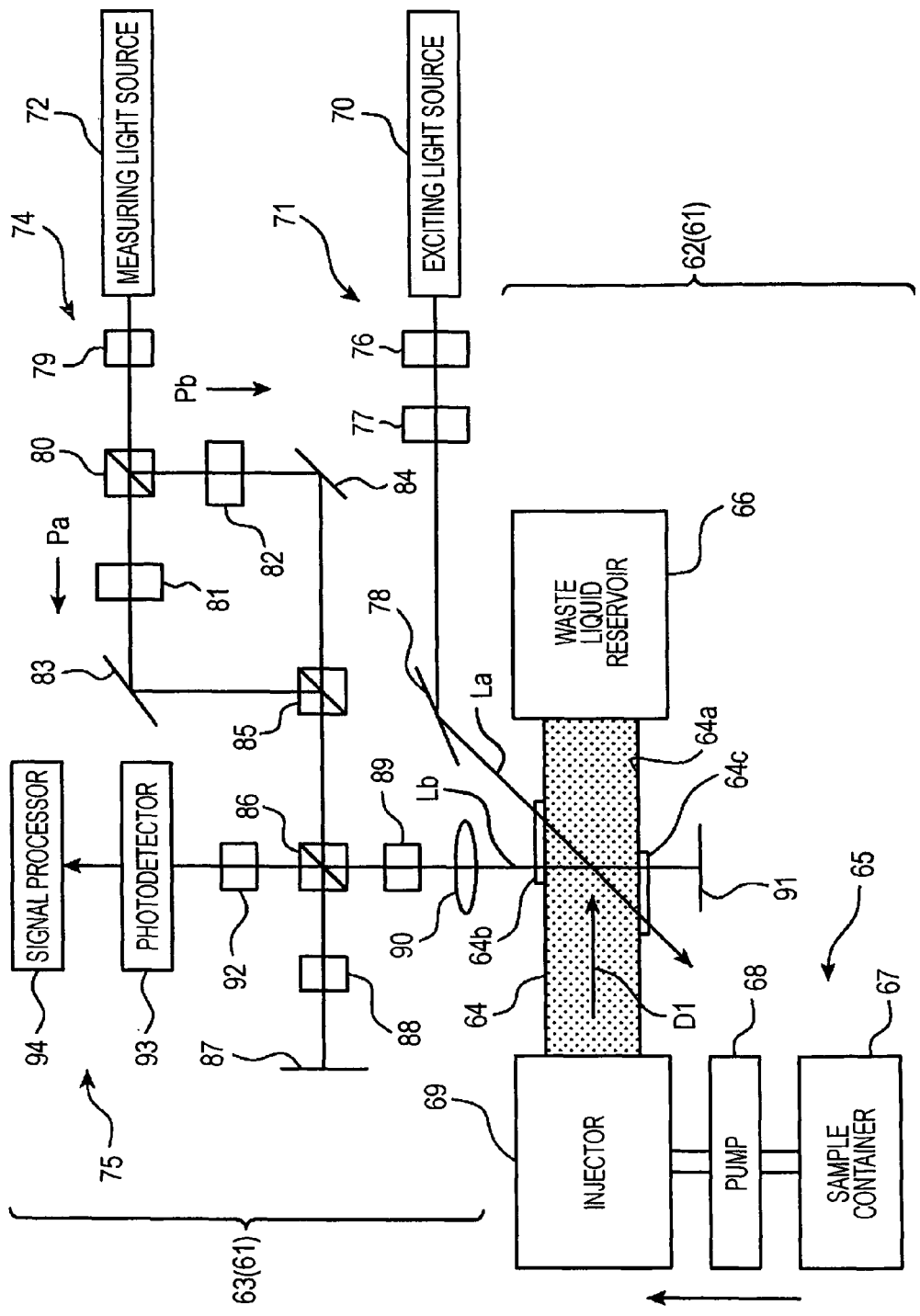
FIG. 5 is a schematic drawing showing the entire configuration of a separation/purification analyzer according to a third embodiment of the present invention.
Figure 6:
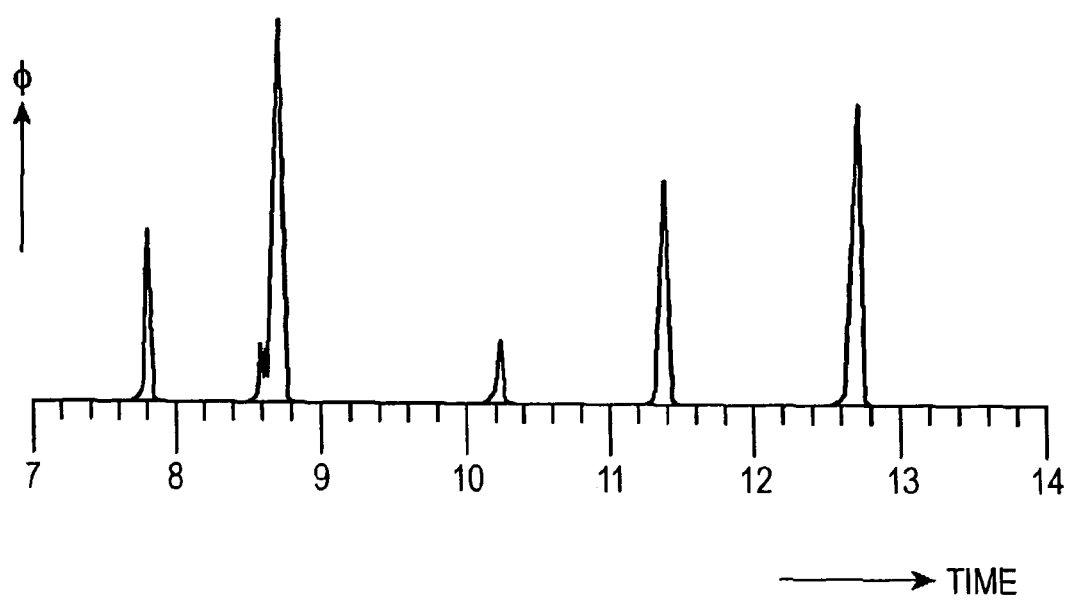
FIG. 6 is a chart showing an example of results obtained using the separation/purification analyzer shown in FIG. 5.

FIG. 5 is a schematic drawing showing the entire configuration of a separation/purification analyzer according to the third embodiment of the present invention.

Referring to FIG. 5, a separation/purification analyzer 61 is provided with a separation purification portion 62 for separating a component to be analyzed from a liquid sample containing a plurality of components, and a detection portion 63 for analyzing the component to be analyzed which has been separated by the separation purification portion 62.

The separation purification portion 62 utilizes the principle of so-called liquid chromatography. Namely, the separation purification portion 62 is provided with a column (separation portion) 64 packed with an adsorbent such as alumina, silica gel, or an ion exchange resin, a supply portion 65 for supplying the liquid sample into the column 64, and a waste liquid reservoir for recovering the liquid sample discharged from the column 64. In this embodiment, the supply portion 65 and the adsorbent charged in the column 64 constitute a purification portion.

The column 64 is a cylindrical member in which a passage 64a with a closed section is formed for filling the liquid sample. In addition, light-transmitting irradiation windows 64b and 64c (each an example of an irradiation position) are provided on the opposite side surfaces of a portion of the column 64 in the longitudinal direction thereof so that light can be transmitted through the liquid sample in the passage 64a through the irradiation windows 64b and 64c from outside the column 64.

The supply portion 65 is provided with a sample container 67 for storing the sample, a pump for sucking the sample from the sample container 67, and an injector 69 for injecting the liquid sample discharged from the pump 68 into the column 64.

When the liquid sample is injected into the column 64 by the supply portion 65, the components contained in the liquid sample flow in the passage 64a with differences in speed corresponding to differences in adsorption rate on the adsorbent. Namely, the components are separated and purified.

On the other hand, the detection portion 63 is capable of quantitatively analyzing the components separated and purified in the column 64.

Specifically, the detection portion 63 includes an exciting light source 70 which emits predetermined exciting light, an exciting light guide portion 71 for guiding the exciting light emitted from the exciting light source 70 to the irradiation windows 64b and 64c and transmitting the exciting light through the liquid sample, a measuring light source 72 which emits predetermined measuring light, a measuring light guide portion 74 for guiding the measuring light emitted from the measuring light source 72 to the irradiation windows 64b and 64c and transmitting the measuring light through the liquid sample, and a phase change measuring portion 75 for measuring a phase change of the measuring light before and after transmission through the liquid sample.

The exciting light source 70 emits light containing an absorption wavelength of a component to be analyzed of the components contained in the liquid sample. For example, when the component to be analyzed is composed of a biological molecule or organic molecule, a mercury xenon lamp or a deuterium lamp is used as the exciting light source 70 because such a molecule has an absorption wavelength in the ultraviolet region of 200 to 400 nm.

The exciting light guide portion 71 includes an interference filter 76 for taking out exciting light having an absorption wavelength of a component to be analyzed (265 nm or 280 nm when the component to be analyzed is a biological molecule or organic molecule) from the light emitted from the exciting light source 70, a chopper 77 for converting the exciting light transmitted through the interference filter 76 to chopped light at a predetermined period, and a mirror 78 for reflecting the exciting light passing through the chopper 77 to the irradiation windows 64b and 64c side so that the exciting light reflected by the mirror 78 is transmitted through the liquid sample through the irradiation windows 64b and 64c along the optical axis La. As a result, the component to be analyzed in the liquid sample absorbs the exciting light and generates heat (produces photothermal conversion), and the refractive index of the liquid sample is changed by the temperature change (increase). In this embodiment, the optical axis La crosses at an inclination angle of about 45° the flow direction D1 of the liquid sample in the column 64.

When a liquid sample containing a biological or organic molecule bonded with a pigment molecule as a marker is analyzed, a pigment molecule having an absorption wavelength in the visible region is generally used. Therefore, a white light source such as a halogen lamp or the like is used as the exciting light source 70 so that exciting light having an absorption wavelength in the visible region (about 360 nm to 830 nm) can be taken out by the interference filter 76.

Means for taking out the exciting light is not limited to the interference filter 76, and for example, spectroscopic means using a prism or an analytical lattice can also be used.

The measuring light source 72 emits light having a wavelength other than the absorption wavelength of the component to be analyzed and the absorption wavelength of a solvent in the liquid sample. For example, a solvent such as water generally does not have an absorption wavelength in the visible region, and thus a He—Ne laser or the like is used as the measuring light source 72 when such a solvent is used. The use of the He—Ne laser can stabilize intensity.

The measuring light guide portion 74 is adapted to separate the light emitted from the measuring light source 72 into two polarized waves Pa and Pb, transmit as the measuring light the polarized wave Pa of the polarized waves Pa and Pb through the liquid sample, guide the polarized wave Pa after the transmission to the phase change measuring portion 75, and guide the polarized wave Pb as the reference light to the phase change measuring portion 75 without transmitting through the liquid sample.

Specifically, in the measuring light guide portion 74, the polarization plane of the light emitted from the measuring light source 72 is modulated by a ½ wavelength plate 79, and further the light is separated into the two polarized waves Pa and Pb perpendicular to each other by a beam splitter 80. Hereinafter, the polarized waves Pa and Pb are referred to as measuring light and reference light, respectively.

The measuring light Pa and the reference light Pb are shifted in frequency (converted in frequency) by acoustooptic modulators (AOM) 81 and 82 and reflected by mirrors 83 and 84, respectively, and then combined together by a polarized beam splitter 85. The frequency difference fb between the perpendicular measuring light Pa and reference light Pb is set to, for example, 30 Mhz.

The reference light Pb of the synthesized light passes through a polarized beam splitter 86, is reflected by a mirror 87, and then returns to the polarized beam splitter 86. The reference light Pb returning to the polarized beam splitter 86 reciprocates in a ¼ wavelength plate 88 disposed between the polarized beam splitter 86 and the mirror 87, and thus the polarization plane is rotated by 90°. Therefore, the reference light Pb is reflected by the polarized beam splitter 86 and guided to the phase change measuring portion 75.

On the other hand, the measuring light Pa is reflected by the polarized beam splitter 86, passes through a ¼ wavelength plate 89 and a lens 90, is guided to the irradiation window 64b, and is incident on the liquid sample through the irradiation window 64b along the optical axis Lb. In this embodiment, the optical axis Lb is set to be substantially perpendicular to the flow direction D1 of the liquid sample in the column 64 and cross the optical axis La in the passage 64a of the column 64.

Further, the measuring light Pa incident on the liquid sample passes through the irradiation window 64c, is reflected by a reflecting mirror 91 provided on the back side of the column 64, is again transmitted through the liquid sample, passes through the lens 90 and the ¼ wavelength plate 89, and returns to the polarized beam splitter 86.

Since the measuring light Pa returning to the polarized beam splitter 86 reciprocates through the ¼ wavelength plate 89 to rotate the polarization plane by 90°, then the measuring light Pa passes through the polarized beam splitter 86, is combined with the reference light Pb, and guided to the phase change measuring portion 75 side.

The phase change measuring portion 75 is provided with a polarizing plate 92 for allowing the measuring light Pa guided from the beam splitter 86 to interfere with the reference light Pb, a photodetector 93 for converting the intensity of the interference light guided from the beam splitter 86 into an electric signal, and a signal processor 94 for executing calculation processing (i.e., measurement of a phase change by a light interference method) of a phase change of the measuring light Pa on the basis of the electric signal output from the photodetector 93.

Like in the above-described embodiment, the intensity S1 of the interference light is represented by the following expression (1):

$$S1 = C1 + C2 \cdot \cos(2\pi \cdot fb \cdot t + \phi) \quad (1)$$

In the expression, C1 and C2 are each a constant determined by the optical systems such as the polarized beam splitter and the transmittance of the liquid sample, $\phi$ is a phase difference due to a difference between the optical path lengths of the measuring light Pa and the reference light Pb, and is fb is a frequency difference between the measuring light Pa and the reference light Pb.

Therefore, according to the expression (1), a difference in the phase difference $\phi$ (change in phase difference) can be calculated by, for example, calculating a difference between the interference light intensity S1 measured under a condition in which a component to be analyzed does not yet flow inside the irradiation windows 64b and 64c and the interference light intensity S1 measured under a condition in which a component to be analyzed flows inside the irradiation windows 64b and 64c.

That is, the difference in the phase difference $\phi$ changes according to the concentration of the component to be analyzed which flows inside the irradiation windows 64b and 64c, and thus a concentration difference of the component to be analyzed which flows inside the irradiation windows 64b and 64c can be determined by measuring the difference in the phase difference $\phi$.

Specifically, the quantity of heat generated of the liquid sample due to absorption of the exciting light increases as the concentration of the component to be analyzed increases, and the refractive index of the liquid sample increases with an increase in the quantity of heat generated. The phase difference $\phi$ between the measuring light Pa transmitted through the liquid sample and the reference light Pb not transmitted through the liquid sample increases as the refractive index increases.

Therefore, for example, a plurality of liquid samples each containing a known concentration of a component to be analyzed is prepared as preliminary test samples, the phase difference $\phi$ is previously measured for the each of the preliminary test samples using the separation/purification analyzer 61, and data of correspondence between the concentration and each phase difference $\phi$ is stored as a data table in the signal processor 94. In this case, the concentration of the component to be analyzed which corresponds to the phase difference $\phi$ measured for the liquid sample to be measured can be determined by interpolation to the data table.

In addition, since the components contained in the liquid sample flow with differences in velocity in the column 64 of the separation purification portion 62, a chart in which peaks of the phase difference $\phi$ appear at different times for the respective component types can be obtained by continuously measuring the phase difference $\phi$. In this chart, the height of a peak of the phase difference $\phi$ shows the concentration of a corresponding component.

As described above, in the separation/purification analyzer 61, the component to be analyzed is excited by irradiation with the exciting light to produce photothermal conversion, and a temperature change of the liquid sample which generates heat in association with the photothermal conversion is measured as a change in refractive index of the liquid sample on the basis of the measuring light Pa after transmission through the liquid sample. Consequently, the component to be analyzed can be quantitatively analyzed.

Namely, in the separation/purification analyzer 61, the analytical precision can be improved by increasing the degree of photothermal conversion. Therefore, even when the component to be analyzed is at a low concentration, high-precision analysis can be performed by increasing the intensity of the exciting light which induces the photothermal conversion.

Therefore, in the separation/purification analyzer 61, the analytical precision can be easily improved by a relatively simple method of increasing the intensity of the exciting light.

Further, as in the embodiment, in a configuration in which the optical axis La of the exciting light and the optical axis Lb of the measuring light Pa are set to be separated, even when a substance which generates heat by the exciting light is arranged on the optical axis La, the measuring light Pa can be led to the liquid sample without being transmitted through the substance. Therefore, it is possible to suppress the occurrence of a phase change of the measuring light Pa due to transmission through the substance which generates heat by the exciting light.

Therefore, according to the embodiment, a phase change can be avoided from occurring in the measuring light Pa due to a cause other than a temperature change of the liquid sample, stabilizing the analytical precision.

Further, according to the embodiment, a lamp light source can be used as the exciting light source 70, thereby suppressing the cost as compared with the use of a laser light source.

In particular, there is known a thermal lens method in which a component to be analyzed is irradiated with exciting light to produce photothermal conversion and form a so-called thermal lens in the liquid sample so that the concentration of the component to be analyzed is detected by measuring the intensity of measuring light transmitted through the thermal lens. However, when the thermal lens method is used, a laser light source is inevitably used.

That is, the thermal lens method requires exciting light with very high intensity which is condensed at a specified position in a liquid sample in order to achieve a thermal lens effect. Therefore, when the exciting light emitted from a lamp light source is condensed by a lens or the like, the exciting light of sufficient intensity cannot be obtained.

On the other hand, in the separation/purification analyzer 61 according to the embodiment, the quantity of heat generated by transmission of the exciting light through the liquid sample can be measured as a phase change by the light interference method based on the measuring light Pa and the reference light Pb. Therefore, the exciting light is not required to be condensed, and consequently, a lamp light source can be used instead of a high-intensity laser light source.

However, this does not mean that a configuration using a laser light source is excluded, and in order to analyze a component to be analyzed which has an absorption wavelength in the visible region, the exciting light with high intensity can be obtained using a laser light source as a white light source instead of the lamp light source.

Further, since exciting light in the infrared region is generally used for measuring a molecular bond state and vibrational level absorption, a halogen lamp or a semiconductor laser can be used as the exciting light source 70. Further, when the exciting light in the far-infrared region is used, a heat source lamp such as a ceramic light source can be used.

In addition, the embodiment is configured to lead the exciting light transmitted through the liquid sample to the outside of the column 64. However, as shown in FIG. 7A, the embodiment may be configured so that the exciting light transmitted through the liquid sample is again transmitted through the liquid sample by a mirror (exciting light reflecting member) 95 provided on the side opposite to the irradiation window 64b with respect to the column 64. Namely, the exciting light guide portion 71 of this embodiment is provided with the mirror 95.

According to this embodiment, the optical path length of the exciting light can be increased by reciprocating the exciting light through the liquid sample, and thus the photothermal effect can be enhanced, thereby increasing the analytical precision.

Further, as shown in FIG. 7B, an optical axis control portion 96 can be provided for holding the mirror 95 rotatably around an axis J1 perpendicular to the optical axes La and Lb so that the crossing point between the optical axes La and Lb can be moved in the passage 64a. The optical axis control portion 96 may be adapted to drive the mirror 78 (refer to FIG. 5).

According to this embodiment, the crossing position between the optical axis La of the exciting light and the optical axis Lb of the measuring light Pa can be controlled, and thus the crossing position can be moved to a position on the higher-concentration side even when the concentration of a component on the peripheral side of a section of the passage 64a is different from that on the central side thereof.

Figure 8:
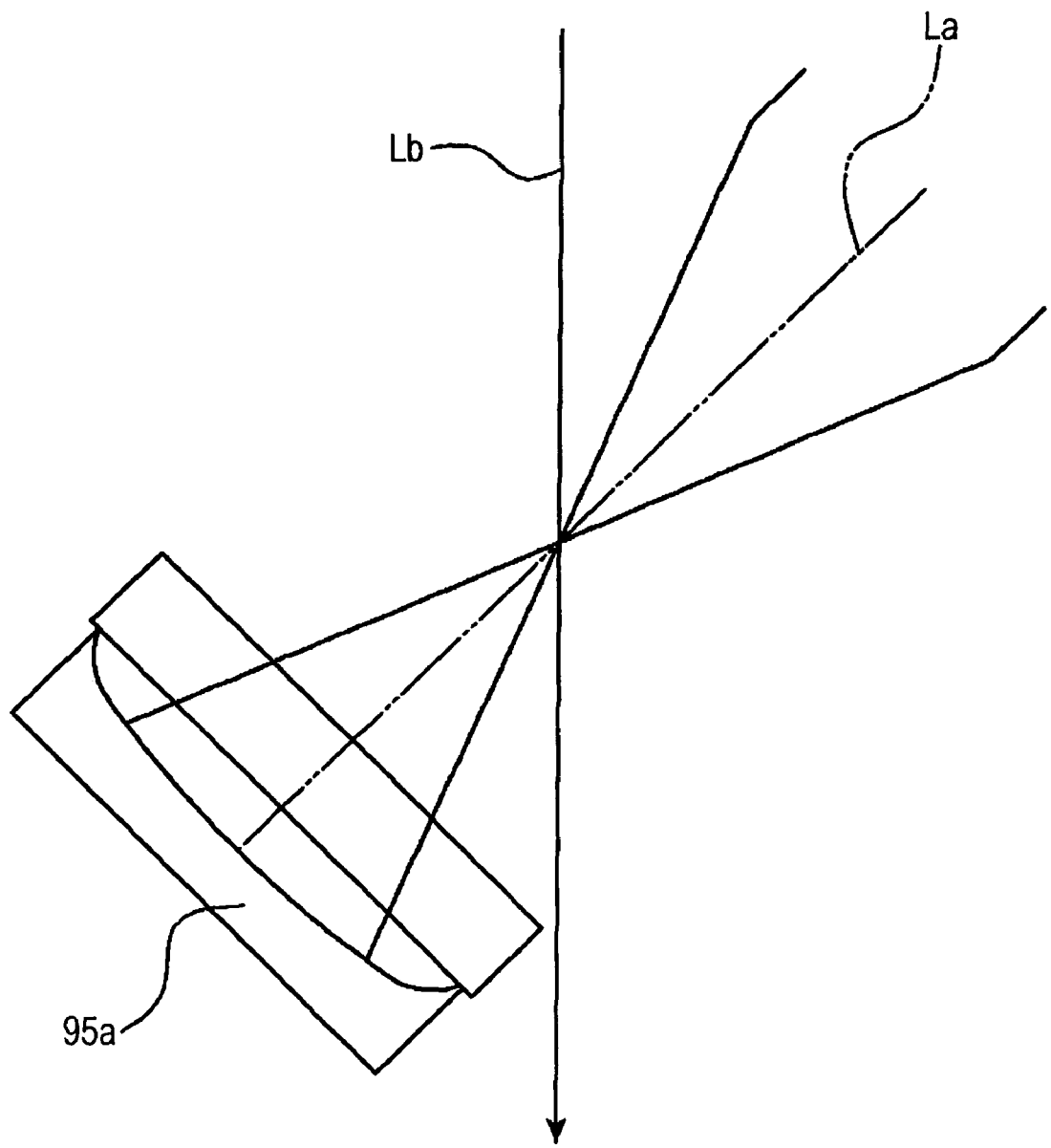
FIG. 8 is an enlarged side view showing a concave mirror of a separation/purification analyzer according to a further embodiment of the present invention.

Further, as shown in FIG. 8, a concave mirror 95a with the focal point arranged on the optical axis Lb of the measuring light Pa may be used as the mirror 95.

According to this embodiment, photothermal conversion on the optical axis Lb of the measuring light Pa can be further increased to further improve the analytical precision.

Figure 9:
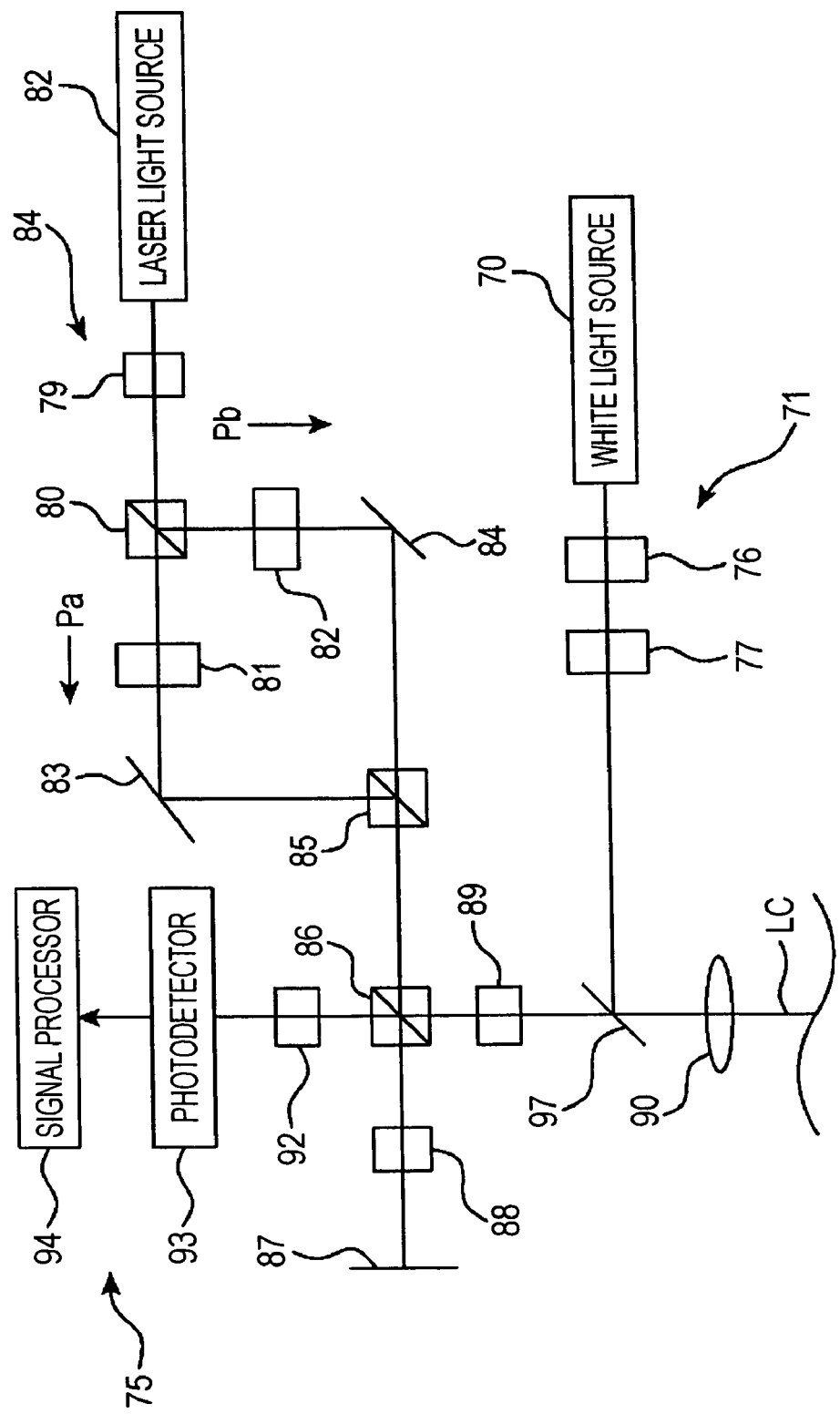
FIG. 9 is a schematic view showing a separation/purification analyzer configured to coaxially apply exciting light and irradiating light according to a further embodiment of the present invention.
Figure 10:
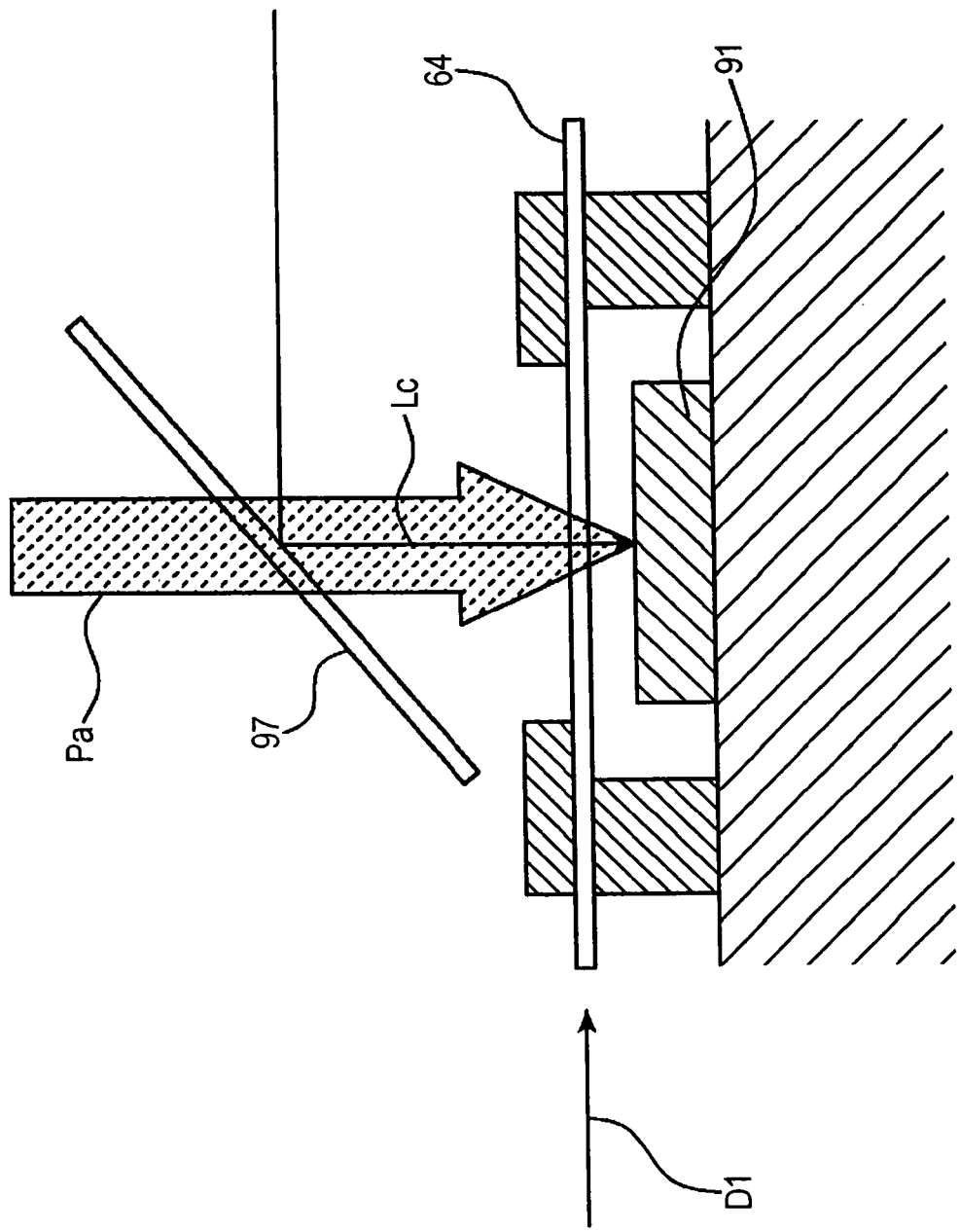
FIG. 10 is an enlarged side view showing the separation/purification portion shown in FIG. 9.

In the embodiment, description is made of a configuration in which the exciting light and the measuring light Pa are incident on the liquid sample along the optical axes La and Lb crossing each other. However, as shown in FIGS. 9 and 10, the exciting light and the measuring light Pa may be coaxially incident on the liquid sample along an optical axis Lc.

Specifically, the exciting light guide portion 71 of this embodiment has a dichroic mirror 97 provided between the ¼ wavelength plate 89 and the lens 90.

The dichroic mirror 97 is configured to transmit the measuring light Pa led from the ¼ wavelength plate 89 but not to transmit the exciting light. Therefore, the measuring light Pa led from the ¼ wavelength plate 89 passes through the dichroic mirror 97, the lens 90, and the liquid sample and is reflected by the reflecting mirror 91. The reflected measuring light Pa again passes through the liquid sample, the lens 90, and the dichroic mirror 97 and is led to the photodetector 93 side.

According to this embodiment, the measuring light Pa can be transmitted over the substantially entire region in which photothermal conversion is produced by the exciting light, and thus the temperature change (phase change) can be obtained as a higher value, thereby further improving the analytical precision.

Figure 11:
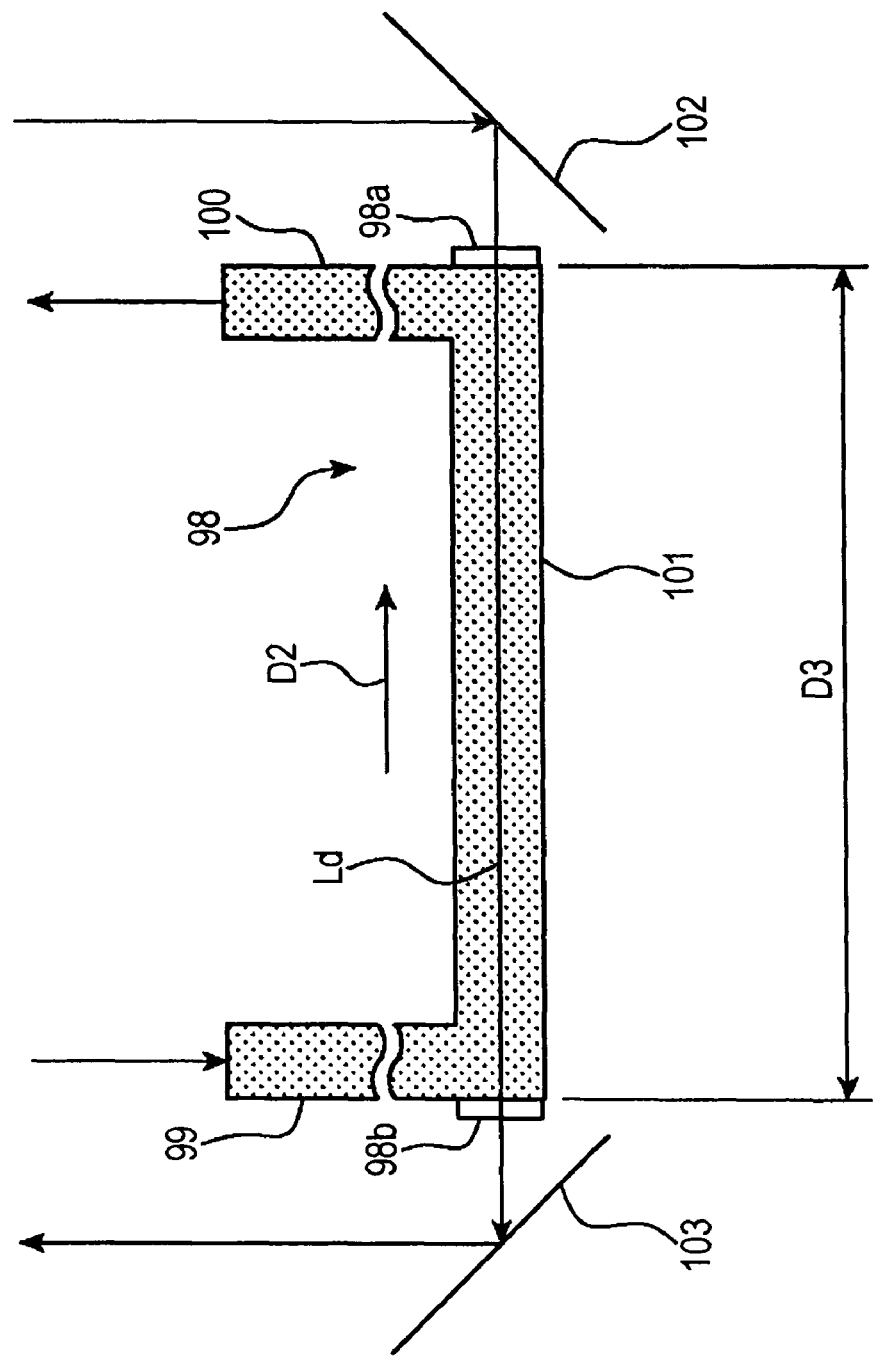
FIG. 11 is an enlarged plan view showing a separation/purification portion according to a further embodiment of the present invention.

Further, when the exciting light and the measuring light Pa are applied along the optical axis Lc, the exciting light and the measuring light Pa are preferably applied along an optical axis Ld substantially parallel to the flow direction D2 of the liquid sample in the column 64 as shown in FIG. 11.

Specifically, the column 98 according to this embodiment is a cylindrical member having a substantially U-shaped planar form and including an entrance-side passage 99 and a discharge-side passage 100 which extend in substantially parallel, and an analytical passage 71 connected to the passages 99 and 100 at right angles.

The length dimension D3 of the analytical passage 71 is determined on the basis of a relation between the flow rate of the liquid sample by the injector (refer to FIG. 5) and the passage lengths of the entrance-side passage 99 and the discharge-side passage 100 so as to cause a period in which the component to be analyzed independently flows.

In addition, the column 98 has light-transmitting irradiation windows 98a and 98b which are provided on both side surfaces of the analytic passage 101 in the longitudinal direction thereof so that light can be applied to the analytical passage 101 through the irradiation windows 98a and 98b from outside the column 64.

On the other hand, the exciting light guide portion 71 and the measuring light guide portion 74 are adapted to guide the exciting light and the measuring light, respectively, along the optical axis Ld substantially parallel to the flow direction D2 of the component to be analyzed which flows in the analytical passage 101.

Specifically, the exciting light guide portion 71 and the measuring light guide portion 74 include mirrors 102 and 103 which are provided on the sides of the irradiation windows 98a and 98b, respectively, so that the exciting light and the measuring light Pa are reflected by the mirrors 102 and 103 to be transmitted through the liquid sample in the analytical passage 101 along the flow direction D1 of the liquid sample in the analytical passage 101. The measuring light Pa reflected by the mirror 103 is led to the photodetector 93 (refer to FIG. 5) side.

According to the embodiment, unlike in the case in which the exciting light and the measuring light Pa are applied in a direction crossing the flow direction D2, the optical path of the exciting light and the measuring light Pa can be increased without increasing the sectional area of the passage 64a.

Figure 12:
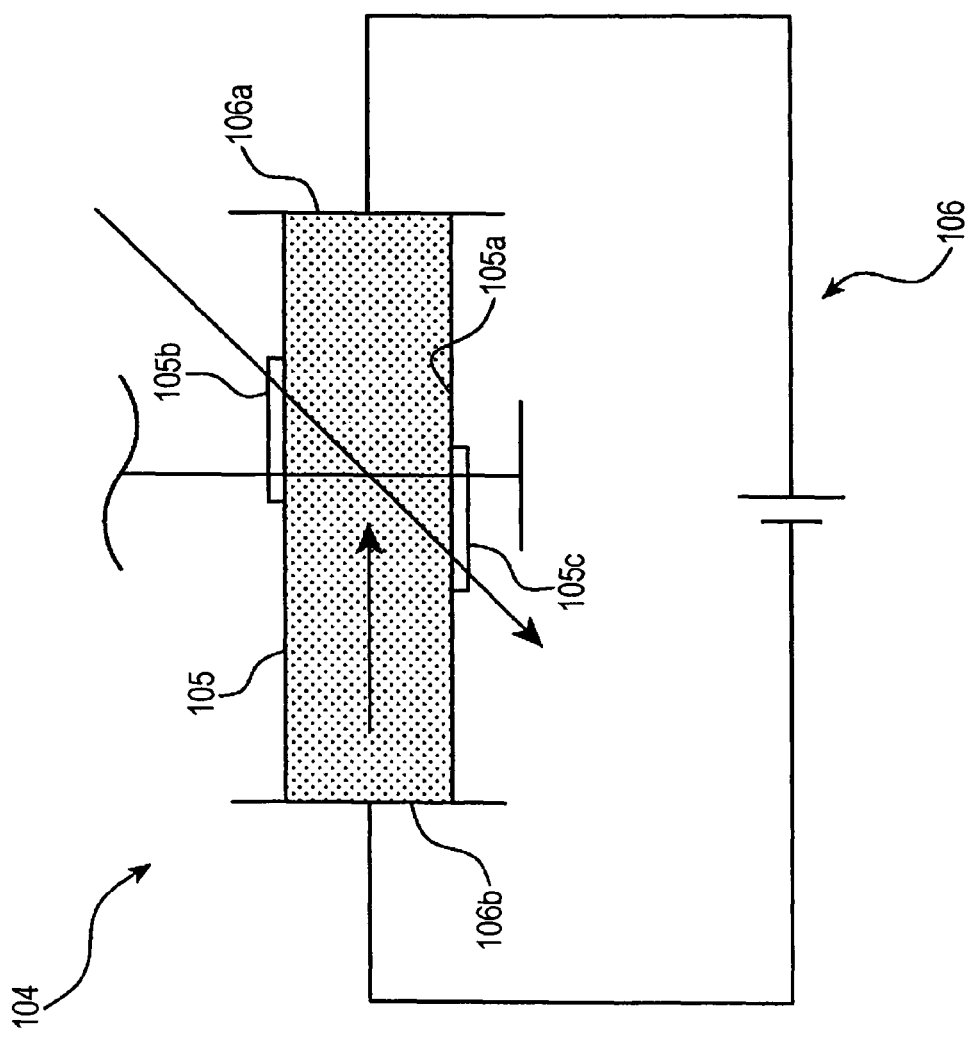
FIG. 12 is an enlarged schematic view showing a separation/purification portion according to a further embodiment of the present invention.

Although, in each of the above-described embodiments, the separation/purification analyzer 61 provided with the separation purification portion 62 which utilizes the principle of so-called liquid chromatography is described, a separation purification portion 104 utilizing electrophoresis may be used as shown in FIG. 12.

Specifically, the separation purification portion 104 is provided with a capillary 105 in which a passage 105a is formed for filling a liquid sample, and a voltage applying portion (purification portion) 106 which has electrodes 106a and 106b provided at both ends of the capillary 105 and which can apply a voltage to the liquid sample in the passage 105a. When a voltage is applied to the liquid sample by the voltage applying portion 106, components in the liquid sample moves in the capillary 105 with speed differences corresponding to differences in electric characteristics (relation between charge and mass).

In addition, light-transmitting irradiation windows 105b and 105c are provided on the opposing side surfaces of a portion of the capillary 105 in the longitudinal direction thereof so that light can be transmitted through the liquid sample in the passage 10a through the irradiation windows 105b and 105c from outside the capillary 105.

A separation purification portion using so-called gel electrophoresis can be used, in which a glass tube used instead of the capillary 105 and having a larger sectional area than the capillary 105 is filled with gel, such as polyacrylamide, as a carrier. In this case, the gel is not limited to be filled in a glass tube, and the gel may be formed between a pair of glass plates so that the liquid sample is charged between the glass plates.

Prior art relating to the third embodiment is described below.

There have been known separation/purification analyzers each including a separation purification portion for separating a specified component from the components contained in a sample using liquid chromatography, gas chromatography, electrophoretic effect, or the like, and a detection portion for detecting the component separated by the separation purification portion.

As such a type of detector, there is a detector which detects absorbance of the component separated by the separation purification portion (for example, Detector for Liquid Chromatography disclosed in Japanese Unexamined Patent Application Publication No. 2003-149135).

However, the detector of Japanese Unexamined Patent Application Publication No. 2003-149135 analyzes the separated component on the basis of the detected absorbance and thus has difficulty in improving analytical precision.

Namely, the absorbance is calculated on the basis of an intensity ratio (transmittance) before and after transmission through the sample, and thus it is necessary to set a long optical path for light transmitted through the sample so that a light intensity ratio to be detected is increased for improving analytical precision.

In order to increase the optical path, it is necessary to increase the passage sectional area of the sample or change the irradiation direction of light with respect to the passage. However, such a change in design becomes a large scale and is restricted by limitations to the space in an apparatus and the like.

The embodiment has been achieved in consideration of the above-mentioned problem, and an object is to provide a separation/purification analyzer capable of easily improving analytical precision.

In order to solve the problem, the embodiment provides a separation/purification analyzer for separating a component to be analyzed from a sample containing a plurality of components and analyzing the separated component, the analyzer including a separation purification portion including a separation portion having a passage formed therein and a purification portion capable of passing the components in the passage with speed differences, and a detection portion for irradiating the sample in the passage with exciting light which has an absorption wavelength of the component to be analyzed and irradiating the irradiation position with measuring light which has a wavelength other than the absorption wavelength of the component to be analyzed to detect a phase change in the measuring light before and after the transmission through the sample.

According to the embodiment, the component to be analyzed is excited by irradiation with the exciting light to produce photothermal conversion, and a temperature change of the sample which generates heat in association with the photothermal conversion is measured as a change in refractive index of the sample on the basis of the measuring light after transmission through the sample. Consequently, the component to be analyzed can be quantitatively analyzed.

Namely, in the separation/purification analyzer according to the embodiment, the analytical precision can be improved by increasing the degree of photothermal conversion. Therefore, even when the component to be analyzed is at a low concentration, high-precision analysis can be performed by increasing the intensity of the exciting light which induces the photothermal conversion.

Therefore, according to the embodiment, the analytical precision can be improved by a relatively simple method of increasing the intensity of the exciting light.

As an embodiment, the detection portion may be configured to include an exciting light source which emits exciting light, an exciting light guide portion for guiding the exciting light emitted from the exciting light source to a predetermined irradiation position in the separation portion and transmitting the exciting light through the sample, a measuring light source which emits measuring light, a measuring light guide portion for guiding the measuring light emitted from the measuring light source to the irradiation position and transmitting the measuring light through the sample, and a phase change measuring portion for measuring a phase change in the measuring light before and after transmission through the sample.

In this case, the exciting light and the measuring light can be guided to the irradiation position from the exciting light source and the measuring light source by the exciting light guide portion and the measuring light guide portion, respectively, and a phase change in the measuring light can be measured by the phase change measuring portion.

Specifically, the measuring light guide portion can be configured to separate the light emitted from the measuring light source into two lights having different frequencies, guide as the measuring light one of the separated lights to the irradiation position, guide the measuring light transmitted through the sample to the phase change measuring portion, and guide the other light as the reference light to the phase change measuring portion, so that the phase change is measured by the phase change measuring portion using a light interference method on the basis of the measuring light transmitted through the sample and the reference light not transmitted through the sample.

In this case, the component to be analyzed can be quantitatively analyzed by measuring a phase difference between the reference light and the measuring light in the phase change measuring portion.

In the exciting light guide portion and the measuring light guide portion, the exciting light and the measuring light are preferably transmitted through the sample along the optical axes which are set to be substantially coaxial.

In this configuration, the measuring light can be transmitted over the substantially entire region in which photothermal conversion is produced by the exciting light, and thus the temperature change (phase change) can be obtained as a higher value, thereby further improving the analytical precision.

Therefore, when the exciting light and the measuring light are coaxially applied, the exciting light guide portion and the measuring light guide portion are configured to apply the exciting light and the measuring light along an optical axis which is substantially parallel to the flow direction of the component in at least a portion of the passage. In this case, unlike in the case in which the exciting light and the measuring light are applied in a direction crossing the flow direction, the optical path of the exciting light and the measuring light can be set to be long without an increase in the sectional area of the passage.

However, in this configuration, it is necessary to set the length of the passage and the flow rate of the component to be analyzed so that only the component flows in at least a portion of the passage.

On the other hand, the exciting light guide portion may be configured to irradiate the sample with the exciting light along a first optical axis, while the measuring light guide portion may be configured to irradiate with the measuring light along a second optical axis crossing the first optical axis within the passage.

In this configuration, the optical axes of the exciting light and the measuring light can be set to be separated. Therefore, even when a substance which generates heat by the exciting light is arranged on the first optical axis, the measuring light can be led to the sample without being transmitted through the substance. Therefore, it is possible to suppress the occurrence of a phase change of the measuring light due to transmission through the substance which generates heat by the exciting light.

Therefore, according to this configuration, a phase change can be avoided from occurring in the measuring light due to a cause other than a temperature change of the sample, thereby stabilizing the analytical precision.

When the exciting light and the measuring light are applied along separate optical axes, the exciting light guide portion is preferably provided with an optical axis control portion for moving the crossing position between the first optical axis and the second optical axis within the passage.

In this configuration, the crossing position between the first and second optical axes can be controlled. Therefore, even when the concentration of a component on the peripheral side of a section of the passage is different from that at the central side thereof, the crossing position can be moved to a position on the higher-concentration side.

The exciting light guide portion preferably includes an exciting light reflecting member which is provided on the side opposite to the incidence position of the exciting light with respect to the separation portion, for reflecting the exciting light transmitted through the sample to reciprocate the exciting light through the sample.

In this configuration, the exciting light can be reciprocated through the sample to extend the optical path of the exciting light, and thus the photothermal effect can be enhanced to improve the analytical precision.

In this case, when the exciting light reflecting member includes a concave mirror with a focal point arranged on the optical axis of the measuring light, the photothermal effect on the optical axis of the measuring light can be further enhanced to further improve the analytical precision.

In the separation/purification analyzer, preferably, the exciting light source is a lamp light source, and the exciting light guide portion is provided with a filter for extracting the exciting light having a specified wavelength from the light emitted from the lamp light source.

In this case, a lamp light source can be used as the exciting light source, thereby suppressing the cost as compared with the use of a laser light source.

In addition, the separation purification portion may be configured to include the separation portion in which the passage having a closed section is formed, and the purification portion including an adsorbent charged in the passage and a supply portion for supplying a liquid sample into the passage. Therefore, when the liquid sample is supplied by the purification portion, the components contained in the liquid sample flow in the passage with velocity differences corresponding to differences in adsorption rate on the adsorbent.

On the other hand, the separation purification portion may be provided with the separation portion in which the passage is formed, and the purification portion for applying a voltage to the liquid sample within the passage at two positions of the passage in the flow direction. When a voltage is applied by the purification portion, components contained in the liquid sample flow in the passage with velocity differences corresponding to differences in electric characteristics.

In this configuration, the component to be analyzed can separated and purified using so-called liquid chromatography or electrophoresis and quantitatively analyzed by the detection portion.

INDUSTRIAL APPLICABILITY

According to the present invention, the concentration of impurities contained in ultrapure water or press water can be efficiently analyzed with high precision.

The invention claimed is:

1. An analyzer for measuring impurities contained in a liquid flowing in a predetermined line, the analyzer comprising:
   a sampling portion which is branched from the line and to which part of the liquid flowing through the line is introduced;
   an exciting light irradiation system for irradiating the liquid introduced into the sampling portion with exciting light;
   a measuring light irradiation system for irradiating, with measuring light different from the exciting light, a measurement object region where a photothermal effect of the impurities is produced by irradiation of the liquid with the exciting light;
   a phase change detector for detecting a phase change of the measuring light transmitted through the measurement object region; and
   a signal processor for outputting a measurement signal about the impurity concentration in the liquid on the basis of a detection signal from the phase change detector,
   wherein the sampling portion is provided with an absorption spectrometric portion which can apply the exciting light and the measuring light in a same direction as a flow of the liquid introduced in the sampling portion, and which comprises a linear pipe.

2. The analyzer according to claim 1, the analyzer being an apparatus for analyzing impurities containing a metal or metal ions,
   wherein the sampling portion includes an absorption spectrometric portion for irradiating with the exciting light and the measuring light and a coloring portion provided upstream of the absorption spectrometric portion, for adding and mixing a reagent to and with the liquid, the reagent producing a complex which absorbs light at a specified wavelength by a chemical reaction with the impurities; and the exciting light irradiation system irradiates the liquid introduced from the coloring portion to the absorption spectrometric portion with light, as the exiting light, at a wavelength which can be absorbed by the complex.

3. The analyzer according to claim 1, wherein the sampling portion includes a branch line connected to the predetermined line and a flow control portion for controlling the flow rate of the liquid flowing in the branch line to a specified flow rate;

the exciting light irradiation system irradiates the liquid flowing through a specified portion of the branch line with the exciting light; and the signal processor calculates the impurity concentration in the liquid on the basis of the weight of the impurities in the liquid, which is determined from the detection signal of the phase change detector, and the flow rate of the liquid which is controlled by the flow control portion.

4. The analyzer according to claim 3, the analyzer being an apparatus for analyzing impurities containing a metal or metal ions, wherein the impurities are composed of a metal or metal ions;

the predetermined line includes an absorption spectrometric portion for irradiating the liquid flowing in the branch line with the exciting light and the measuring light and a coloring portion provided upstream of the absorption spectrometric portion;

a reagent addition portion is connected to the coloring portion, for adding and mixing a reagent to and with the liquid at a flow rate corresponding to the flow rate of the liquid, the reagent producing a complex which absorbs light at a specified wavelength by a chemical reaction with the impurities;

the exciting light irradiation system irradiates the liquid flowing in the absorption spectrometric portion with light, as the exiting light, at a wavelength which can be absorbed by the complex; and the signal processor calculates the impurity concentration in the liquid on the basis of the weight of the impurities in the liquid, which is determined from the detection signal of the phase change detector, the flow rate of the liquid, and the flow rate of the reagent added.

5. The analyzer according to claim 1, wherein the exciting light irradiation system irradiates with light with a periodically modulated intensity as the exciting light; and the signal processor takes in the detection signal of the phase change detector with timing synchronizing with the period of the intensity modulation.

6. The analyzer according to claim 1, wherein the phase change detector includes a spectroscopic optical system for separating reference light from the measuring light and allowing the reference light to interfere with the measuring light transmitted through the measurement object region and a photodetector for detecting the intensity of the interference light.

7. The analyzer according to claim 1, wherein the phase change detector includes light reflecting portions disposed opposite to each other on both sides of the measurement object region provided therebetween, and a photodetector;

one of the light reflecting portions reflects part of the measuring light transmitted through the measurement object region toward the other reflecting portion to reciprocate the measuring light; and the photodetector receives the measuring light transmitted through at least one of the light reflecting portions toward the side opposite to the measurement object region and detects the intensity of the measuring light.

8. The analyzer according to claim 7, wherein the phase change detector includes a distance control mechanism for controlling the distance between the light reflecting portions in a direction of maintaining the resonant condition of light reciprocating between the light reflecting portions.

\* \* \* \* \*